United States Patent [19]

Stewart et al.

[11] Patent Number: 5,351,117
[45] Date of Patent: Sep. 27, 1994

[54] SENSING A NARROW FREQUENCY BAND AND GEMSTONES

[75] Inventors: Andrew D. G. Stewart, Ashampstead; Robin W. Smith, Croydon; Martin P. Smith, Wargrave; Martin Cooper, Marlow; Christopher M. Welbourn, Maidenhead; Paul M. Spear, Reading, all of England

[73] Assignee: Gersan Establishment, Liechtenstein

[21] Appl. No.: 31,585

[22] Filed: Mar. 15, 1993

Related U.S. Application Data

[60] Division of Ser. No. 810,355, Dec. 18, 1991, Pat. No. 5,206,699, which is a continuation of Ser. No. 349,265, May 8, 1989, abandoned.

[30] Foreign Application Priority Data

| May 6, 1988 | [GB] | United Kingdom | 8810723.0 |
| May 6, 1988 | [GB] | United Kingdom | 8810724.8 |
| Jul. 5, 1988 | [GB] | United Kingdom | 8815941.3 |
| Jul. 7, 1988 | [GB] | United Kingdom | 8816156.7 |
| Jul. 7, 1988 | [GB] | United Kingdom | 8816157.5 |
| Jul. 7, 1988 | [GB] | United Kingdom | 8816164.1 |
| Jul. 7, 1988 | [GB] | United Kingdom | 8816165.8 |
| Jul. 7, 1988 | [GB] | United Kingdom | 8816167.4 |
| Nov. 9, 1988 | [GB] | United Kingdom | 8826225.8 |
| Mar. 23, 1989 | [GB] | United Kingdom | 8906853.0 |

[51] Int. Cl.$^5$ ............... G01N 21/65; G01N 21/87
[52] U.S. Cl. ............................ 356/30; 356/301
[58] Field of Search .............. 356/301, 307, 30; 209/576, 577, 578, 579, 589

[56] References Cited

U.S. PATENT DOCUMENTS

| 3,736,428 | 5/1973 | Monroe. | |
| 3,971,951 | 7/1976 | Rikukawa et al. | |
| 4,030,827 | 6/1977 | Delhaye et al. | |
| 4,195,930 | 4/1980 | Delhaye et al. | 356/301 |
| 4,200,801 | 4/1980 | Schuresko. | |
| 4,212,397 | 7/1980 | Bockelmann. | |

(List continued on next page.)

FOREIGN PATENT DOCUMENTS

| 0056426 | 9/1981 | European Pat. Off. |
| 60-11313 | 6/1985 | Japan. |
| WO88/01378 | 2/1988 | PCT Int'l Appl. |

(List continued on next page.)

OTHER PUBLICATIONS

"Optical Engineering", Mar./Apr. 1985, vol. 24 No. 2 Duncan et al, pp. 352–355.
"Journal of Raman Spectroscopy", vol. 17, pp. 415–423 Everall et al (1986).

(List continued on next page.)

*Primary Examiner*—F. L. Evans
*Attorney, Agent, or Firm*—Kerkam, Stowell, Kondracki & Clarke

[57] ABSTRACT

In order to sort diamond-bearing ore particles conveyed on a wide belt, exciting radiation strikes the belt along an extended line. Diamonds are detected by passing the emitted radiation through a narrow band pass filter and sensing the Raman radiation with a photo-multiplier tube. Only axial-parallel rays passing through the filter reach the photo-multiplier tube. An array of side-by-side converging lenses can be used, the lenses being of rectangular shape as seen looking along the optical axis with their long axes at right angles to the line of radiation. The ore particles are in the plane of the foci of the lenses, so that radiation emitted by each particle is passed in parallel rays through the filter. In order to stop rays having an angle of incidence greater than the maximum permitted, to avoid identifying non-diamond material as diamond, a further converging lens is used to focus the rays at the plane of a telecentric stop. The stop stops rays having too great an angle of incidence. The position of the diamond can be detected for instance by a CCD array or by a time domain technique. The apparatus can be monitored by giving a signal when the radiation from tracer stones and holes on either side of the belt, differs from predetermined values.

15 Claims, 15 Drawing Sheets

U.S. PATENT DOCUMENTS

| | | |
|---|---|---|
| 4,275,299 | 6/1981 | Favre . |
| 4,365,153 | 12/1982 | Seigel et al. . |
| 4,407,008 | 9/1983 | Schmidt et al. . |
| 4,619,528 | 10/1986 | Genack et al. . |
| 4,632,550 | 12/1986 | Hara et al. . |
| 4,678,277 | 7/1987 | Delhaye et al. . |
| 4,693,377 | 9/1987 | Gerrard et al. . |
| 4,704,522 | 11/1987 | Hirai et al. . |
| 4,799,786 | 1/1989 | Gerrard . |

FOREIGN PATENT DOCUMENTS

| | | |
|---|---|---|
| 1384813 | 2/1975 | United Kingdom . |
| 2089029 | 6/1982 | United Kingdom . |
| 2140555 | 11/1984 | United Kingdom . |
| 2199657 | 7/1988 | United Kingdom . |

OTHER PUBLICATIONS

"Journal of Physical and Scientific Instruments", 19 (1986) Howard et al, pp. 934–943.

"Analytical Chemistry", vol. 46, No. 2, Feb. 1974, Van-Duyne et al, pp. 213–222.

"Anal. Chem", 1985, Demas et al, pp. 538–545 vol. 57, No. 2.

"Rev. Sci. Instrum." 56 (6) Jun. 1985 (American Instit. of Physics, Watanabe et al, pp. 1195–1198.

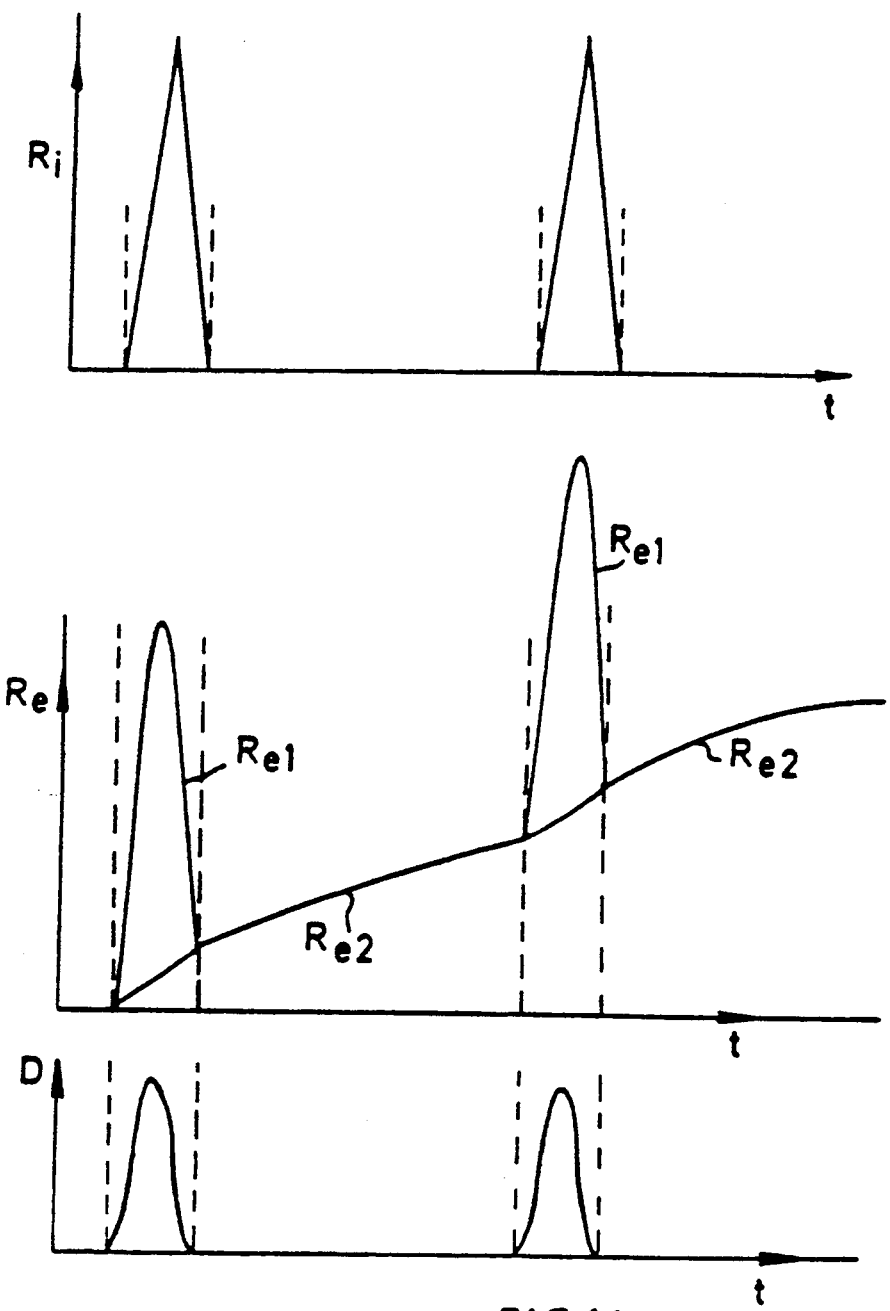
FIG.14.
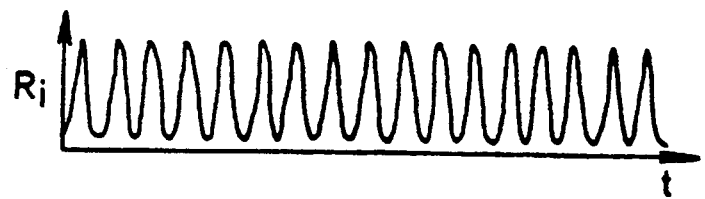
FIG.15.
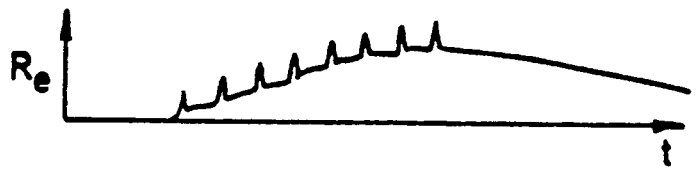

SENSING A NARROW FREQUENCY BAND AND GEMSTONES

This is a division of application Ser. No. 07/810,355 filed Dec. 18, 1991, now U.S. Pat. No. 5,206,699, which is a continuation of application Ser. No. 07/349,265, filed May 8, 1989, now abandoned.

BACKGROUND OF THE INVENTION

This invention relates generally to examining objects or zones. In one aspect, the invention relates to sensing (i.e. detecting) a selected narrow frequency band of radiation which can be received from any point along an extended line, using narrow spectral band filtering (narrow band pass filter means). The invention is more particularly but not exclusively for identifying specific discrete objects or specific zones of an article. The invention was developed for sorting gemstones, and specifically diamonds, from gemstone-bearing ore; it may be applicable to sorting other gemstones or minerals, such as emeralds, rubies or zircons. However, the invention can be used as a general technique for examining a large area, and less generally can be applied to identifying any suitable discrete objects, or can be applied to general inspection techniques such as inspecting paper sheet material or quality control of castings or turbine blades, or examining metals for impurities, e.g. slag in steel, or detecting a gap in an anti-reflection coating on glass or in a diamond film on a loudspeaker cone, or examining filleted fish for freshness or the presence of bones (using ultra-violet radiation).

Much of the remainder of the description is particularly concerned with sensing or detecting Raman radiation on excitation with visible laser radiation, but the invention is applicable to any suitable exciting radiations, such as X-ray, visible, infra-red or ultra-violet radiation, produced by any suitable means. The emission can be detected in any suitable direction relative to the incident radiation, e.g. in the same direction (back illumination) or in the opposite direction (front illumination).

It is known that when certain materials are irradiated, in addition to scattering the incident radiation, they emit radiation in the form of broad band fluorescence (wavelengths longer than the excitation wavelength), and in discrete frequencies which are different from the incident rodation due to the Raman shift. The Raman frequency bands (called the Stokes and the anti-Stokes) are equally spaced on either side of the frequency of the incident radiation: the frequency differences are uniquely characteristic of a material. These Raman emissions enable e.g. diamond to be identified and sorted from other materials such as spinel, calcite and zircons. Although there are two Raman frequencies, one normally looks at the lower frequency (longer wavelength) Stokes emission as it has the greater intensity under normal operating conditions.

Normally, the exciting radiation not only causes the diamond Raman emissions, but also excites other luminescences. The gauge does not exhibit Raman emission with a frequency shift characteristics of diamond. However gauge, and some diamonds, emit other wavelength radiation or fluorescence, and this gives considerable problems in identifying only the Raman radiation and hence the diamonds. The Raman emission is very weak, and can be completely swamped by the other emitted radiations.

The possibility of using the Raman shift to sort or identify diamonds has been described in general terms in for instance GB-A-2 140 555, GB-A-2 199 657, WO 86/07457 and WO 88/01378.

Another problem with using the Raman shift is that as the Raman emission is very weak, a large aperture lens or other collection means must be used to capture the maximum amount of Raman radiation—in general, one needs a lens of say f1 or less. A further problem is that if the method is to be used commercially, large numbers of objects must be sorted per unit time, or large areas of the articles must be scanned per unit time; for example, when sorting ore, one should be able to sort ore which is travelling on a belt at least 0.3 m wide and generally say 1 m or 2 m wide—the particles of ore can occupy a wide path in other ways, for instance if sliding, falling or in free flight or if carried in a liquid stream. Very generally, it is desirable to be able to sort particles or objects moving in a path whose width can accommodate a number of the particles or objects. WO 86/07457 does not deal with this problem, as it is concerned with the identification of a diamond by a jewellet. GB-A-2 140 555 and GB-A-2 199 657 describe ore sorting, but the machinery used requires the ore to be fed along a narrow belt so that the ore particles are lined up in the direction of travel, and each particle is passed through the optical axis of the viewing means. WO 88/01378 uses a multiplicity of optical paths to cover a wide conveyor chute, each path being confined and being its own detector.

Normally, the exciting radiation not only causes the Raman emissions, but also excites the general background radiation. The Raman radiation is also in a very narrow band, so it is possible to reduce general background radiation using a commercially-available narrow band pass filter having a narrow pass band. In this context, "narrow" has its normal meaning as used in this art. However, more specifically, it can mean selecting a band of wavelengths which, on an energy/wave length curve, extends approximately from half-amplitude on one side of the emission being examined to half amplitude on the other side. For the invention, and particularly for Raman, the band will normally be of the order of 1 nm, say 1 nm or 2 nm, and is most unlikely ever to be greater than 10 nm. For other-photoluminescence, the band could be approximately 20, 30 or 40 nm. The filters used, particularly for narrow band filtering, will normally be interference filters where the band is transmitted; in theory at least, a reflected narrow band could be sensed. Narrow band pass filters are also called line filters.

A narrow band pass filter however passes its design pass frequency on its axis (zero angle of incidence), but passes slightly different frequencies off its axis. This is illustrated in FIG. 1 of the accompanying drawings. In other words, the pass frequency of the filter depends upon the angle of incidence and it is necessary for all rays to pass through the filter nearly parallel to the axis, one quoted maximum divergence being $\pm 4°$—in practice, the specific angle depends upon how sensitive the detection should be, and wider or narrower divergences may be acceptable. If rays pass through the filter at greater angles, it is possible for non-diamond material to be identified as diamond material. This does not give a problem when the objects are on the optical axis, but it does give a considerable problem when the objects are distributed over a relatively wide area. More generally, there is a danger, when sorting objects or marking defective zones of an article, that the wrong object or zone is selected due to picking up an oblique emission from an object or zone, of the wrong but adjacent wave length.

The Invention

According to a first aspect, the invention is concerned with irradiating a line across the objects or article, and the line is viewed with a viewing system including narrow band pass filter means which, within a specific angle of incidence, substantially filter out all but a narrow frequency band which is being detected. Sensing means sense radiation which is passed through the filter means, and there are means for preventing rays outside said angle of incidence reaching the sensing means thus the rays outside said angle of incidence can either be prevented from passing through the filter means, or, if they pass through the filter means, can be prevented from reaching the sensing means. To scan the objects or article, the irradiating means and viewing means can be moved relative to the objects or article in a direction generally transverse to said line. The invention can be applied to identifying or sorting diamonds or other specific luminescing materials in ore particles moving in a path whose width is capable of accommodating a number of the particles, e.g., on a wide belt.

In one particular arrangement, there are collection means which allow to pass through the filter means both rays which are within said angle of incidence and rays which are outside said angle of incidence, and means for stopping any rays which have passed through the filter means outside said angle of incidence.

In use, the collection means will extend along and substantially parallel to the line being examined (though some non-parallelity may be tolerated, e.g. up to ±4°). The collection means, or at least its first component, can be any suitable component, even a simple slot. A limited sector of radiation (as seen looking at 90° to said line) passes through the narrow pass band filter means and is not stopped. The invention enables all radiation being examined to pass through the narrow band pass filter means at an angle of incidence acceptably close to zero, say within ±4°. After the narrow pass band filter means, normal optics can be used.

One collection means is a stack or array of lenses: large aperture or low f number systems can be stacked close together—each lens can have an f number of 0.5 along its length, i.e. at right angles to the said line, and 7 across its width. It is possible to use a stack of glass lenses, but Fresnel lenses are preferred as they allow a lower f No. system to be designed. The collection means could be different, e.g. a stack of mirrors or a holographic grating—such a grating can be formed by producing multiple holograms all falling within the f number constraint, taking light from a number of points along a line and transmitting the light along a certain beam angle.

The stack or array is compact and easy to manufacture, but has disadvantages, namely: overlap or periodicity occurs at the junctions of lenses or the like; to reduce the effect of periodicity, the system can only be defocussed away from the lens, limiting the effective depth of focus which is important if large lumps are being examined.

An alternative to the array of lenses is to use a cylindrical lens or the equivalent. This avoids the disadvantages referred to above. The cylindrical lens effect could be achieved by a normal lens, a Fresnel lens, a mirror or a holographic grating.

In another arrangement, there are forming means which, as seen looking at 90° to the line of radiation, form radiation from any point on the line into substantially parallel rays within said specific angle of incidence, and pass substantially parallel rays through the filter means.

Although examining along a line is referred to herein, it is in theory possible to examine an area having substantial width as well as length, using a suitable collection means, the line then just being one of many lines which together form the width. In general, the line need not be rectilinear.

As indicated above, the invention is not restricted to using visible wavelengths for the exciting radiation, or to utilising a Raman emission for the identification of the objects or zones. For instance, the exciting radiation can be X-rays, for example using a collimated wedge to give a wide fan of energy along said line, or even scanning along the line with say a galvo-scanner having a grazing incidence X-ray mirror; or can be ultra-violet or infra-red radiation, scanned along the line. If there is a long time constant after radiation (e.g. diamonds irradiated with X-rays), in a system where the objects or article quickly move out of the viewing zone, pre-radiation may be used to pre-excite the luminescence mechanism.

Any means can be used for selecting, identifying or indicating the specific objects (or zones) which are indicated by the selected frequency radiation sensing means. When sorting, the preferred way is to use a series of air jets spaced across the path of the objects, but other ways of ejecting can be used. Alternatively an ink or other marking system could be used; when inspecting an article, an ink marking system is a suitable system. Physical removing or sorting is not essential. In some circumstances, the particles need only be counted, e.g. to determine what percentage of the particles is present, or the particles may be tagged in some way.

The intensity of the anti-Stokes Raman signal is, at room temperature, calculated as being approximately one three-hundredths of the intensity of the Stokes signal. This made the anti-Stokes signal very unattractive, particularly having regard to the fact that the Stokes signal itself is very weak; it is difficult to capture sufficient Raman radiation for examination of an object.

According to a second aspect, it has been found that the use of the anti-Stokes signal can be advantageous in the particular cases of identifying gemstones, e.g. diamonds, or of examining gauge for picking out gemstones. The background competing luminescence from e.g. the diamond itself may be significantly reduced on the shorter wave-length (higher energy) side of the incident radiation wave-length, resulting in an improved Raman signal to background ratio. In other words, at the wave-lengths detected, there is less broad band luminescence from the diamond itself. The lessened contamination enables one to use slightly wider band width optical filters in an optical detection system, for instance reducing the necessity to avoid off-axis incident radiation. Furthermore, detection instruments, such as photo-multiplier photocathodes, have enhanced sensitivity at shorter wave-lengths.

The material being sorted can be heated, which increases the relative strength of the anti-Stokes signal.

It would be possible to look at both Raman signals simultaneously, and in this way obtain additional discrimination.

According to a third aspect, the invention provides for examining a large number of objects distributed over an area or examining an article, by irradiating a line across the area or article in order to excite luminescence, inducing relative movement between the position of the line and the area or article, to scan the area or article, and detecting emitted luminescence using detecting means responsive to the location from which the luminescence is emitted, to thereby identify the location of a specific object or zone.

Though the first and second aspects are primarily concerned with sorting diamonds from gauge on an extended belt, the third aspect is more applicable to sorting minerals in general and particularly for sorting minerals other than diamond from gauge: the minerals must luminesce in some way.

Thus, it is possible to image across the belt using e.g. an intensified CCD (charge coupled device) array or position-sensitive photo-multiplier tube which acts as the detecting means and can, for instance, give positional information to a microprocessor for actuating a line of ejectors to eject diamond material. If the optical collection and conversion efficiencies are suitable, and if the response time is acceptable, it is possible to use say the intensified CCD array as the only luminescence detector. This is cost-effective, and easy to maintain.

An advantage of this aspect is that it can be used in arrangements in which the exciting radiation is not scanned across a line, but the whole line is permanently irradiated, for instance as in an X-ray recovery machine.

The exciting radiation can be any suitable radiation, for instance X-ray, ultra-violet or visible laser, and the emitted luminescence which is detected can be any suitable luminescence, not necessarily in the visible spectrum. If X-rays are used, the broad band luminescence produced can be examined through broad band filtering.

It is highly desirable to have on-line or self calibration, or monitoring, so that a signal is given when the performance changes, e.g. due to lenses becoming dirty, or the laser output changing or the photo-multiplier working incorrectly. This is not only applicable to the present invention and can be applied to any suitable examination technique involving line scanning, e.g. a colour scan or a U.V. scan.

According to a fourth aspect, the invention provides monitoring means which include scanning means for scanning incident radiation along a line, the monitoring means including a first zone on the line which emits radiation when it receives the incident radiation, a second zone on the line which absorbs substantially all or a large proportion of the incident radiation and emits little, or substantially no, radiation, at least in a predetermined frequency band, when it receives the incident radiation, and sensing means for sensing radiation emitted from the first zone and from the second zone, and giving a signal when the radiation sensed from either zone differs from predetermined values.

According to a fifth aspect of the invention, it is possible to have separate means for detecting the existence of a specific luminescence and for identifying the position of the luminescence. The latter means can give positional information to a microprocessor for actuating a line of ejectors to elect diamond material. This enables narrow band pass filtering to be used for the detector which detects the existence of the specific object or zone, with a single very sensitive detector, and wider band pass filtering to be used for the detecting means which detect position. The sensitive detector would be expensive, but the position detecting means can be relatively cheap.

This aspect can be used in arrangements in which the exciting radiation is not scanned across a line, but the whole line is permanently irradiated, for instance as in an X-ray recovery machine.

The exciting radiation can be any suitable radiation, for instance X-ray, ultra-violet or visible laser, and the emitted luminescence which is detected can be any suitable luminescence, not necessarily in the visible spectrum. The weaker luminescence will usually be in a narrow band. The preferred luminescences for diamonds are Raman luminescence (the Stokes or the anti-Stokes emission) as the weaker luminescence, which is weak but specific to diamonds, and general background luminescence, which is stronger but also emitted by e.g. zircons.

Relating to a sixth aspect, one problem is to identify the position in the scan line from which emitted radiation is sensed or detected. It would be possible to use a large number of side-by-side sensors, but this is expensive.

According to the sixth aspect, information can be obtained from a modulating exciting stimulus by changing the frequency of modulation of the stimulus, sensing the response, and detecting the frequency of the response. More specifically, this can be used to identify objects or zones of an article by projecting modulated radiation to strike the objects or zones along an extended line with the modulation frequency of the incident radiation changing along the line.

The method of the sixth aspect is broadly usable wherever information is required from a response to an excitating stimulus, particularly if the response is radiation-emitting (e.g. optical); the method is particularly useful when positional information is required.

In the preferred embodiment, the incident radiation is modulated, and the modulation is changed along the line, the frequency of response being identified. This enables the position of the article or zone emitting the significant radiation to be identified using a single sensor or detector; however, it is possible to use a number of side-by-side detectors, each detector responding to a certain length of the line. The invention can simplify the electronics; time division multiplexing can be used.

The method can be used with any suitable emitted radiation, e.g. ultra-violet, laser or X-ray; however, the modulation frequency must be compatible with the rise/decay time or life time (luminescence reaction time) of the emitted radiation. Thus stones such as diamonds and zircons can be sorted from gangue using general luminescence, which has a relatively long life time, or diamonds alone can be sorted from gangue using Raman luminescence, which has a very short life time.

The incident radiation can be provided by a single source (e.g. a laser with a rotating polygonal mirror to provide a scan), and the modulation frequency can be ramped up or down from end to end of the line (the frequency being changed in time and space). Alternatively, a number of sources can be used, each irradiating a short length of the line, e.g. laser diodes operating at different pulse frequencies (the frequency being changed in space alone). Different responses from the same location could be identified if the frequency changes in time alone.

A seventh aspect of the invention enables specific objects or zones to be identified by detecting emitted luminescence using a detecting means in which the response is located in dependence on the location of an object or zone emitting luminescence, and scanning the response of the detecting means in order to determine the location from which the luminescence was omitted by the position of the scan at the incident of detection of the emitted luminescence.

This aspect is particularly applicable to sorting diamonds and other luminescing minerals from gangue on a wide belt (or just after projection from the end of the belt), but is generally applicable. The aspect is particularly useful in arrangements in which it is difficult or impractical to scan the exciting radiation across a line, for instance where X-radiation is used. The exciting radiation can be any suitable radiation, for instance X-ray, ultra-violet or visible laser, and the emitted luminescence which is detected can be any suitable luminescence, not necessarily in the visible spectrum.

Particularly in this aspect, pre-radiation may be used to pre-excite the luminescence mechanism.

An eighth aspect relates to identifying gemstones, in which incident or exciting radiation is projected onto the particle in question, the emitted radiation is detected, and the gemstone is identified according to the radiation emitted. This aspect can be used to examine single particles or a number of particles along an extended line. However, this aspect can be used as a general technique for examining and can be applied to identifying any suitable discrete objects or to general inspection techniques.

The eighth aspect provides a way of identifying a gemstone by irradiating the gemstone with modulated radiation to cause the emission of radiation having a short rise and/or decay time, and detecting a signal which is modulated at a frequency corresponding to the frequency of modulation of the exciting radiation. This can be used to identify gemstones among gangue particles which are moving in a wide path, by irradiating a line across the path.

This aspect provides better discrimination from competing luminescence (e.g. to sort diamonds from zircons) and background luminescence. There is no need for e.g. beam splitters to detect and subtract the background luminescence. It may also be possible to have larger apertures or larger pass bands in the viewing system, and hence greater radiation capture.

Raman radiation (Stokes or anti-Stokes) is distinguished from the other emitted radiations by the very fast rise and decay times, or life time of Raman emissions—the life time of the Raman event is about 3 ps, though at this speed the times are substantially affected by the transit time through the diamond itself and hence by the size of the diamond: the luminescence rise and decay times, or life times, for diamonds and certain minerals which one expects to find in diamond-bearing gangue are generally between 3 ns and 10 ms. Although not limited to such values, this aspect can be used to detect emitted radiations having life times from 3 ps to 100 msec, say, depending on the type of sort being carried out and the radiation to be detected: luminescence lifetimes will in general be of the order of nanoseconds up to of the order of tens of nanoseconds. For diamond and other objects and zones, any luminescence can be detected which has a rise, decay or life time shorter than that luminescence emitted by competing material and which would pass through any filtering used: it should be noted in this context that e.g. when sorting diamonds from gangue, it is acceptable if some lumps of gangue are also sorted out with the diamonds.

The use of delay times in examining samples has been disclosed in U.S. Pat. Nos. 4,632,550, and 4,786,170, an article by Van Duyne et al in "Analytical Chemistry", Vol. 46, No. 2, pp 213–222, an article by Everall et al in "Journal of Raman Spectroscopy", Vol. 17, pp 414–423, an article by Watanabe et al in "Review of Scientific Instrument", 56 (6), pp 1195–1198, and an article by Howard et al in "Journal of Physical and Scientific Instruments", 19, pp 934–943.

In practice, the exciting radiation can be modulated at a frequency of say 10 MHz to 1 GHz. The radiation emitted by the object or zone being examined will try and follow the modulated exciting radiation and is detected e.g. with a detector having a rise time response of say about 0.2 ns. Thus the invention exploits the very short life time of say the Raman signal compared to the relatively long life times of other luminescence processes; a good signal would be obtained from the Raman emission and lower signals from the other luminescence as the other luminescence would not be fully active due to its relatively long rise time constants. In a preferred system, the exciting radiation is modulated such that the time interval of the modulation is short compared to the rise or decay time of the luminescence emission. A detection system and associated electronics can process the signals and select and eject material according to luminescent rise/decay time or life time criteria. In a general sense, the detector should provide a signal which is modulated at a frequency corresponding to the incident radiation frequency; to do this, the detector itself could in theory be switched on and off or made effective and ineffective, or its output signal could be chopped, at a frequency normally equal to the incident radiation frequency (though e.g. a multiple of the pulse frequency is in theory possible). In practice, it is preferred to keep the detector on and determine whether it is giving a signal containing a modulation burst at the incident radiation frequency; the modulation burst is following the e.g. Raman emission. In efffect, by using phase sensitive and other detection techniques, it is possible to detect the Raman emission as the AC component of the signal. The background fluorescence will be the DC component of the detected signal.

Some form of narrow band pass filtering may be required as other materials present may also have luminescence of a similar life time, but at a different wave length. However, in general, much more of the emitted radiation can be collected using the invention. A wide aperture viewing system can be arranged so that the angle of incidence on the narrow band pass filter means is within acceptable limits.

The exciting radiation can be modulated by pulsing (chopping), e.g. sinusoidal or triangular. This may be achieved by using an external modulator or a mode-locked laser. In general, the exciting radiation can have any suitable form.

It is possible to operate with more than one modulation frequency and/or laser wavelength to perform multiple sorting (or object or zone identification) or alternatively strengthened discrimination, on the basis of different decay or life time modes: a multiple sort could for instance be for diamonds, emeralds and rubies. This could be done with a single source of exciting radiation, or with more than one source irradiating the same location, and employing beam splitting to detect the different frequencies - the exciting radiation can contain different wavelengths, e.g. by projecting with two different lasers. Alternatively, the objects or zones can be sequentially irradiated and/or detected.

According to a ninth aspect of the invention, specific objects or zones can be identified e.g. when in relative motion by detecting emitted luminescence at a first time, detecting emitted luminescence at a second time, after the first time, and sensing a difference in the emitted luminescence at the two times.

This aspect exploits variation of spectral output with time, and specifically the different rise/decay time or life time mechanisms associated with diamond and gangue. Time separation is required, and this is preferably achieved by movement though for instance time switching detectors could be used for a single particle system. Thus it would be possible to detect the luminescences sequentially from a single location. If objects or particles are travelling along a belt, two optical systems can be positioned to view the same particle but at different points down the belt separated by a distance equivalent to a known time interval, each optical system having a suitable detector. The signal from the first detector is recorded when a suitable particle passes by, and a second signal is captured from the same particle further along the belt. The variations in the threshold/ratio signals as a function of time can then be calculated and used to identify whether the particle is a e.g. diamond. For instance, if the first detector gives a signal and the second detector does not, the decay time is short and the emission is likely to be a Raman emission associated with diamonds (this depends on the time interval various separations can be used for different luminescences, for instance 10 ns or 10 ms). Although the method may not positively identify diamonds, it can produce a concentrate which is very valuable economically.

In its simplest form, this aspect can be performed transporting the material using a V-belt with two simple optical systems—the particles travel along a single straight line. However, a wide belt could be used with suitable optical systems; positional stability of the material on the belt would be required, and this can be achieved for instance using longitudinal segmented grooves. The detection could be carried out in flight, provided the particles have sufficient positional stability.

Any suitable luminescence emission can be used, provided the differing rise/decay times (for instance associated with pre- and post-dense media separator gangue feed material) are sufficiently different to provide a useful sort; the radiation need not be in the visible spectrum. The exciting radiation can be any suitable radiation such as X-ray, ultra-violet, infra-red or visible laser.

This aspect can rely on a change in absolute signal level, or a change in spectral content, or both, as a function of time.

Any of the aspects of the invention can be combined, if suitable.

PREFERRED EMBODIMENTS

In the embodiments of the invention described below, a large number of objects are distributed over an area, which is in effect rectangular and is shown as the surface of a belt though the objects could be moved in other ways. As the belt moves relative to (and at right angles to) the irradiated line, the whole area is scanned. The same effect occurs when examining an article.

The invention will be further described, by way of example, with reference to the accompanying drawings, in which.

Figure 2:
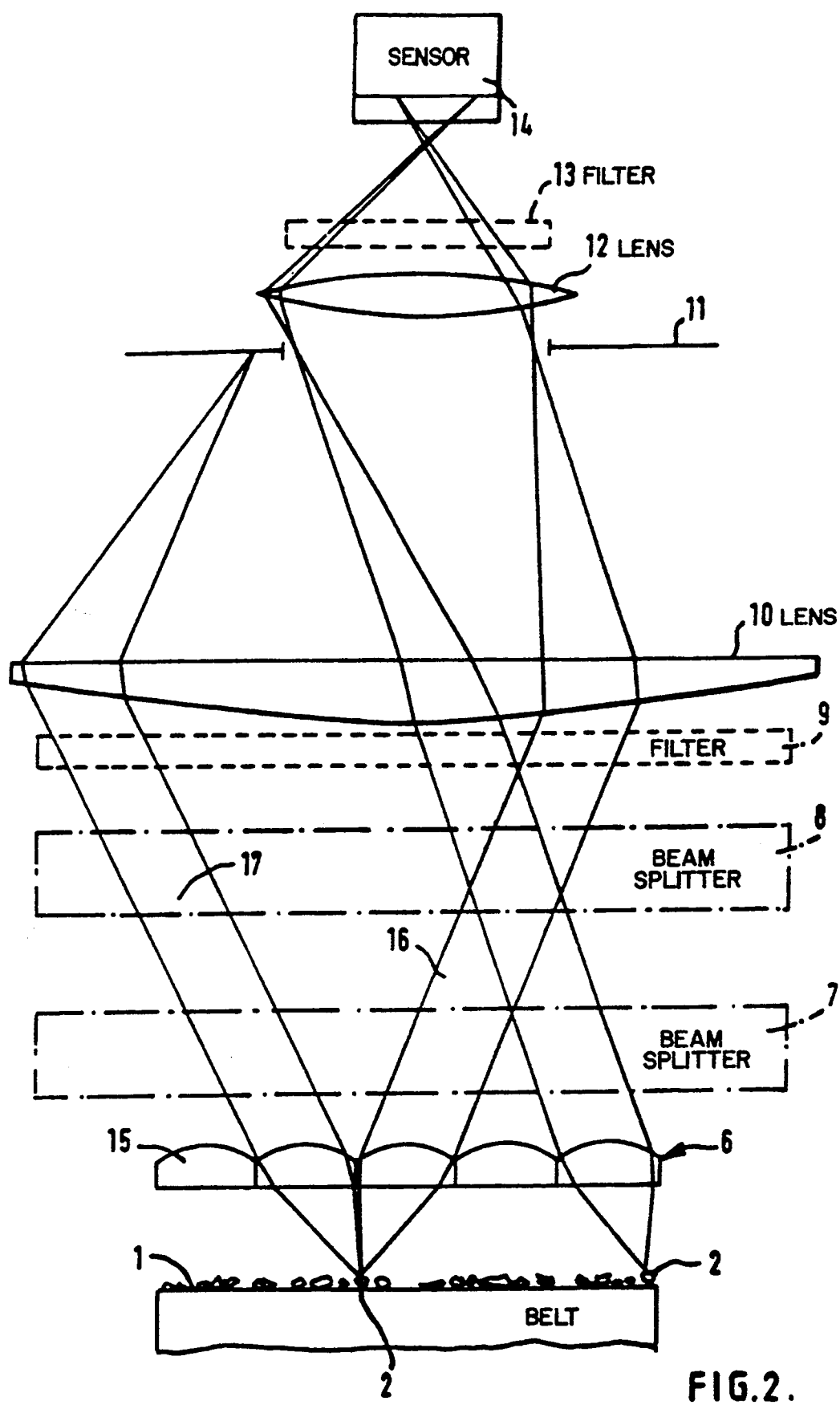
FIG. 2 is a schematic side view of a first apparatus.
Figure 4A:
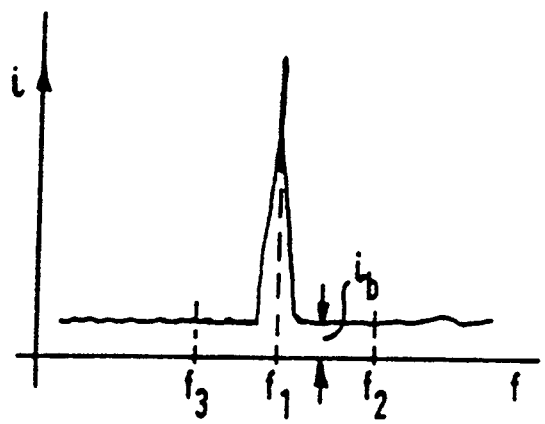
Figure 4B:
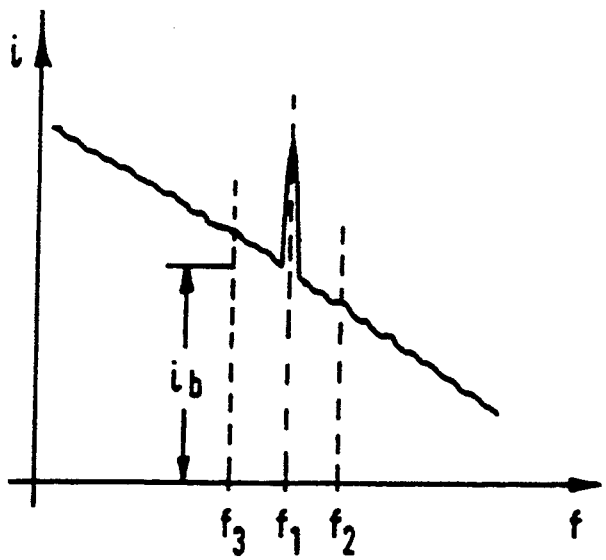
Figure 4C:
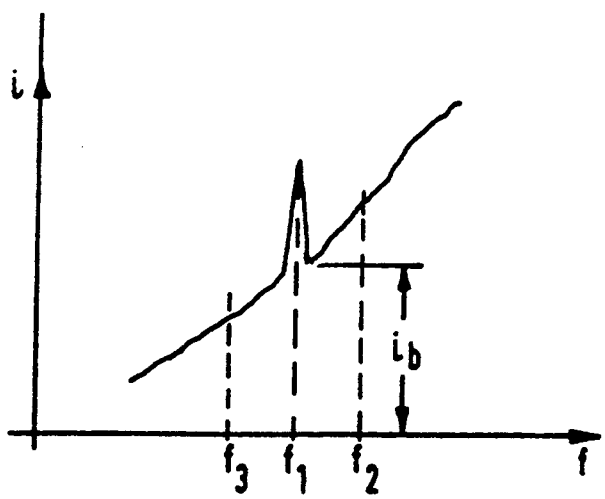
Figure 5:

FIGS. 4a, 4b, and 4c are three alternative radiation spectra;

FIG. 5 illustrates the output of the PMT (photo-multiplier tube) of FIG. 2.

Figure 6:
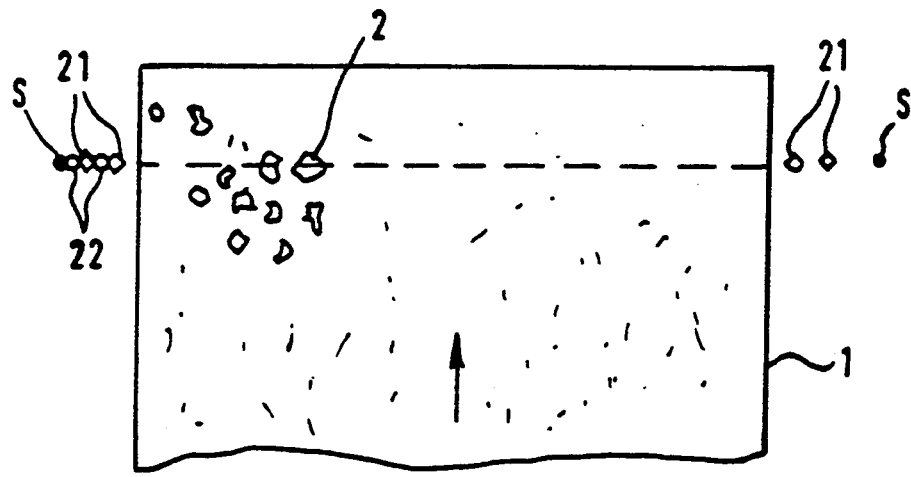
Figure 7:
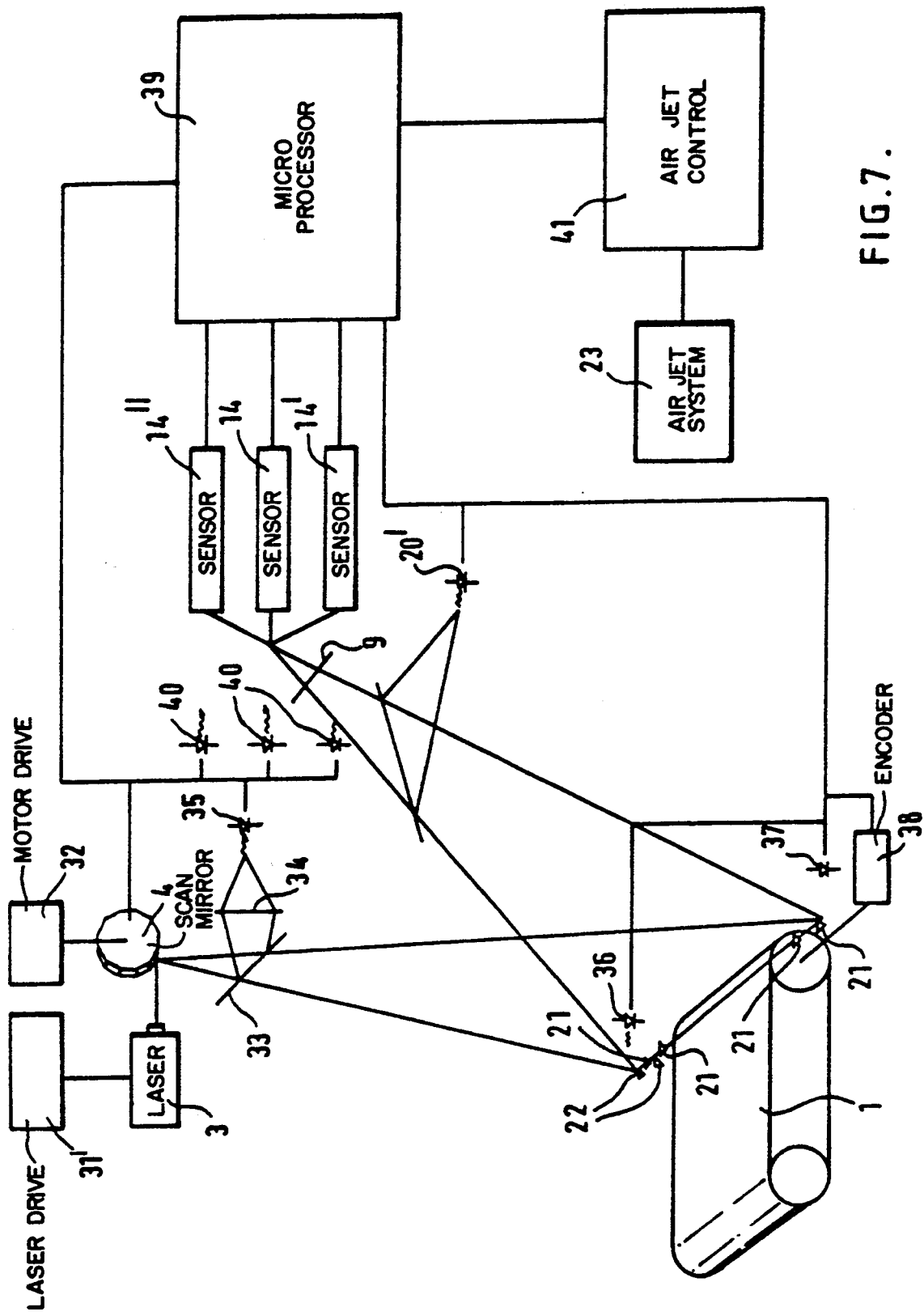
Figure 8:
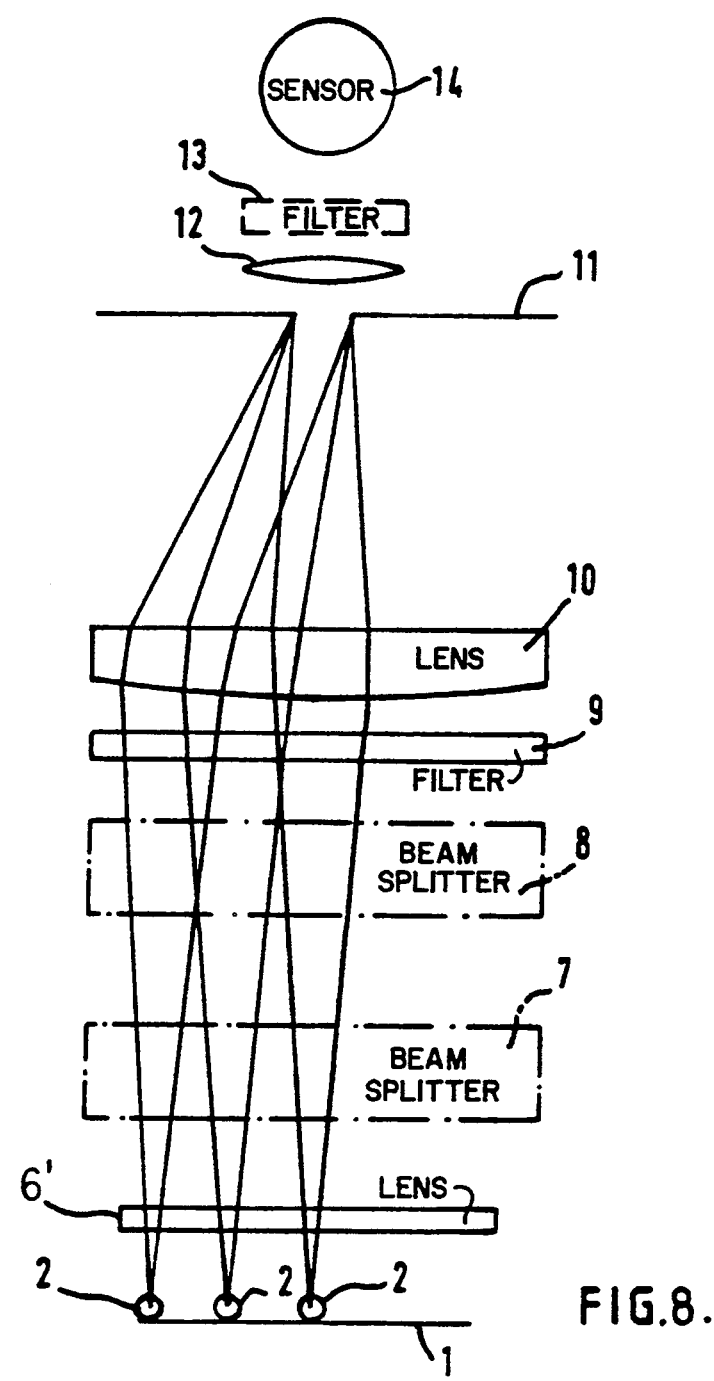
Figure 9:
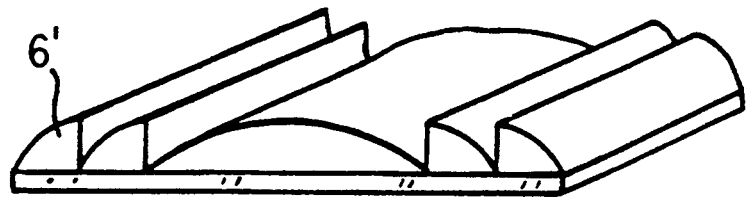
Figure 10:
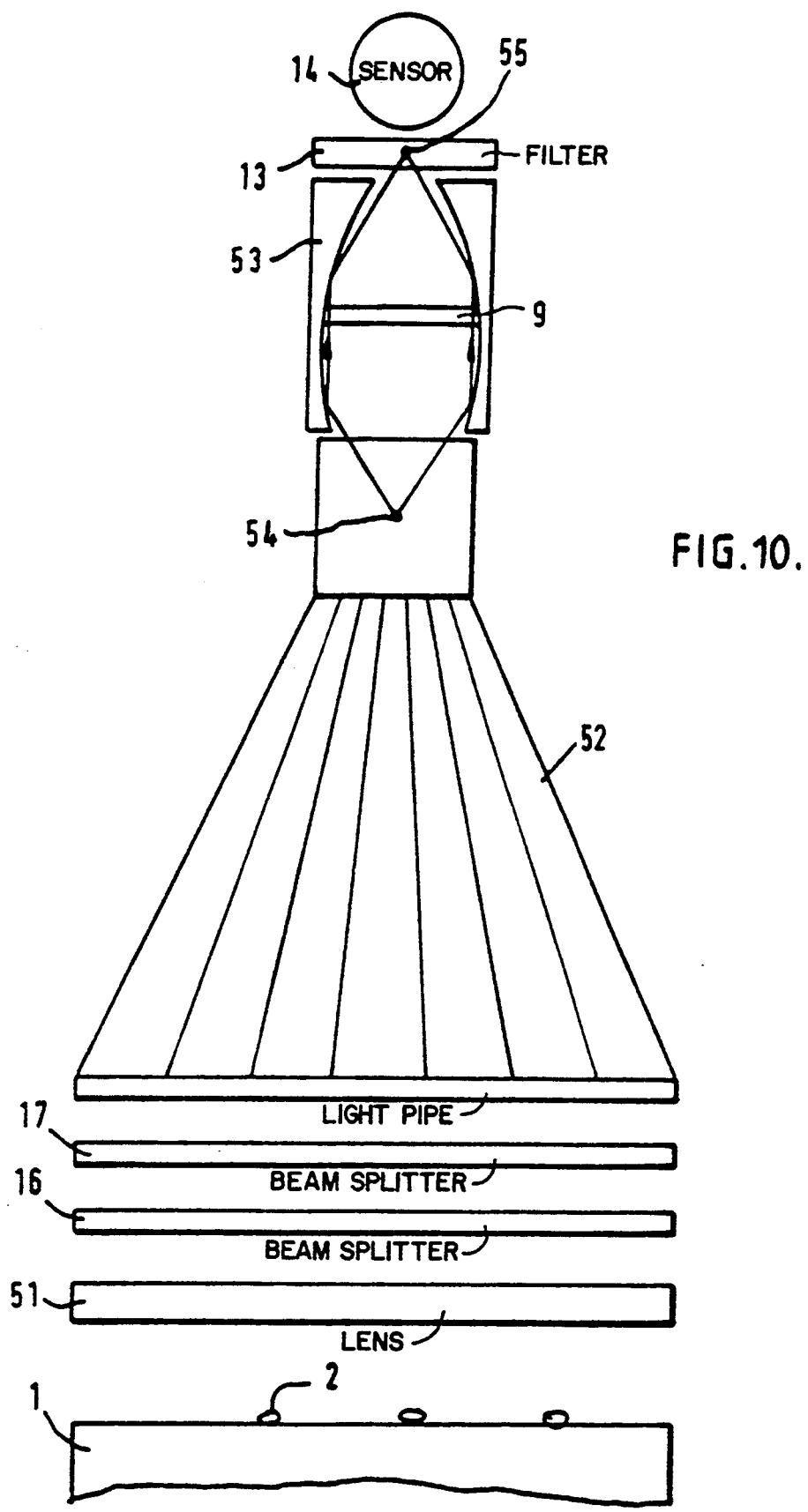
Figure 11:
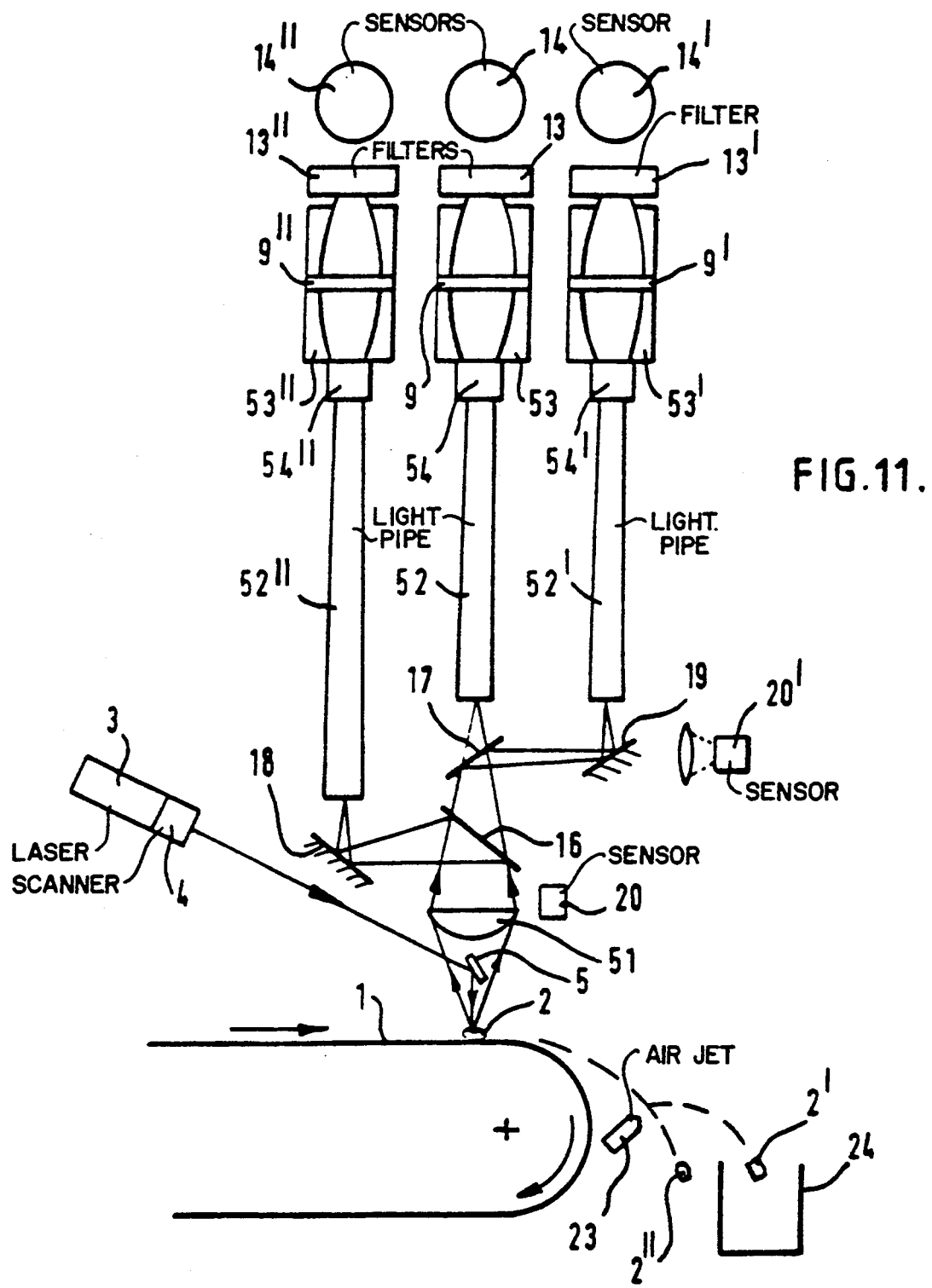
Figure 12:
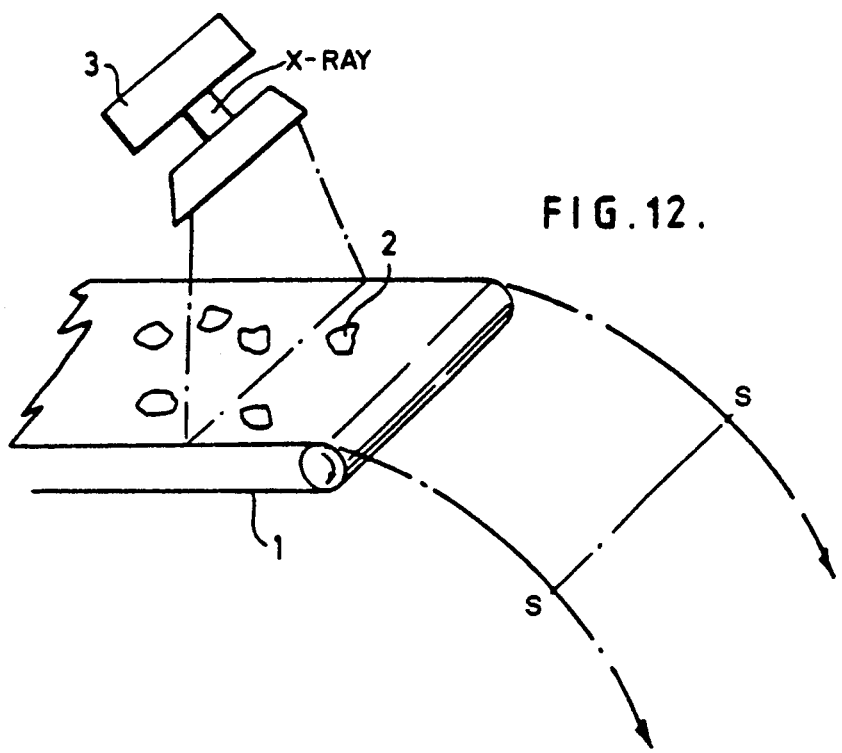
Figure 13:
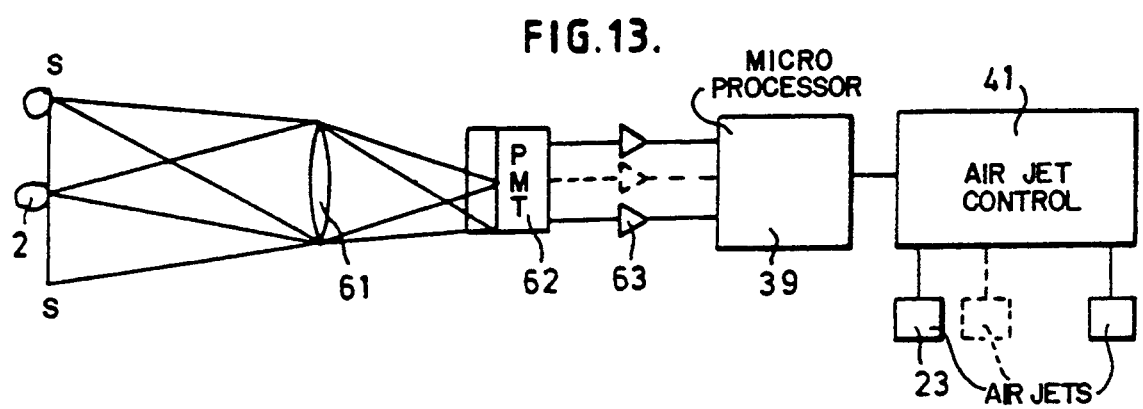
Figure 16:
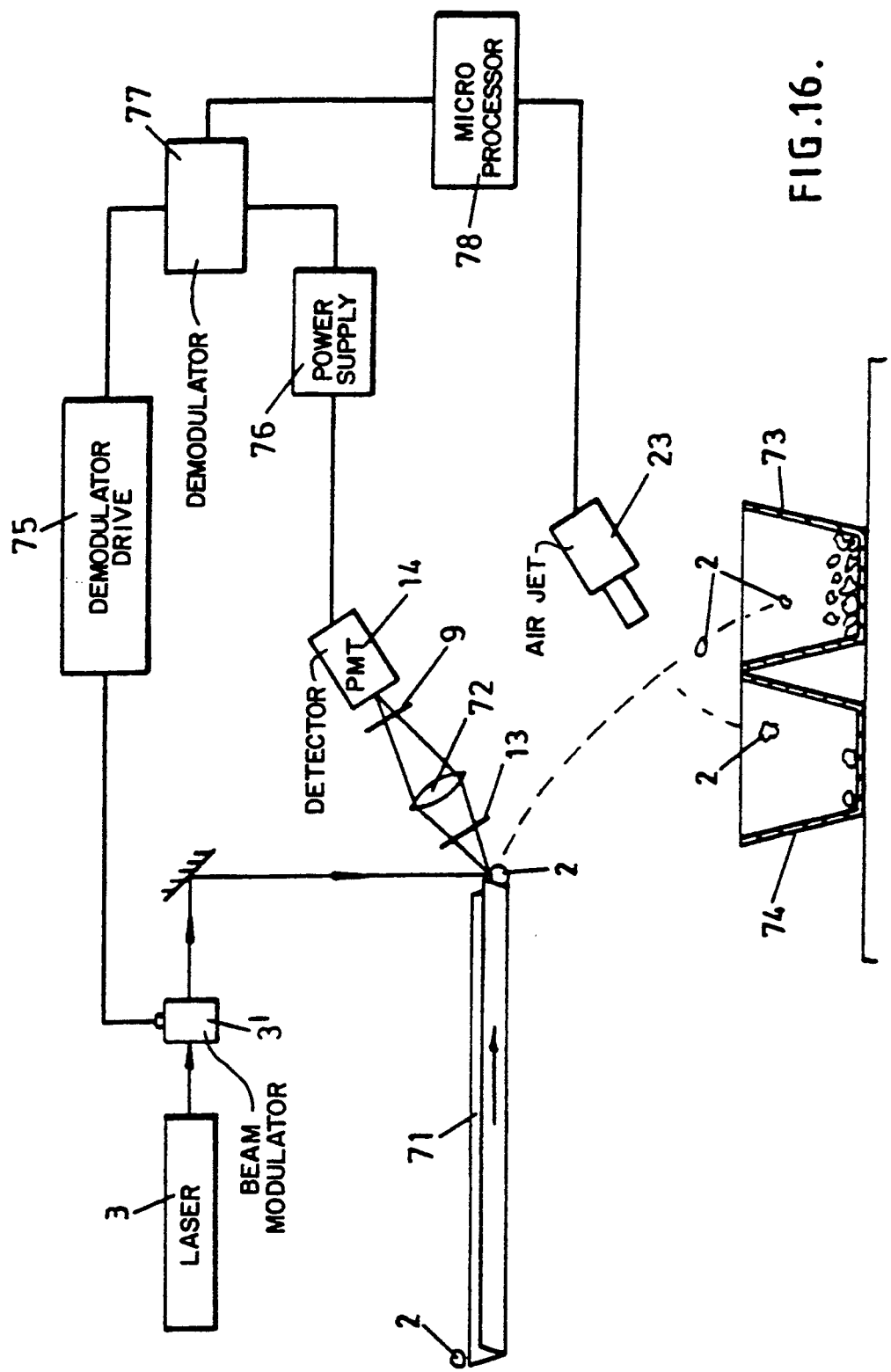
Figure 17:
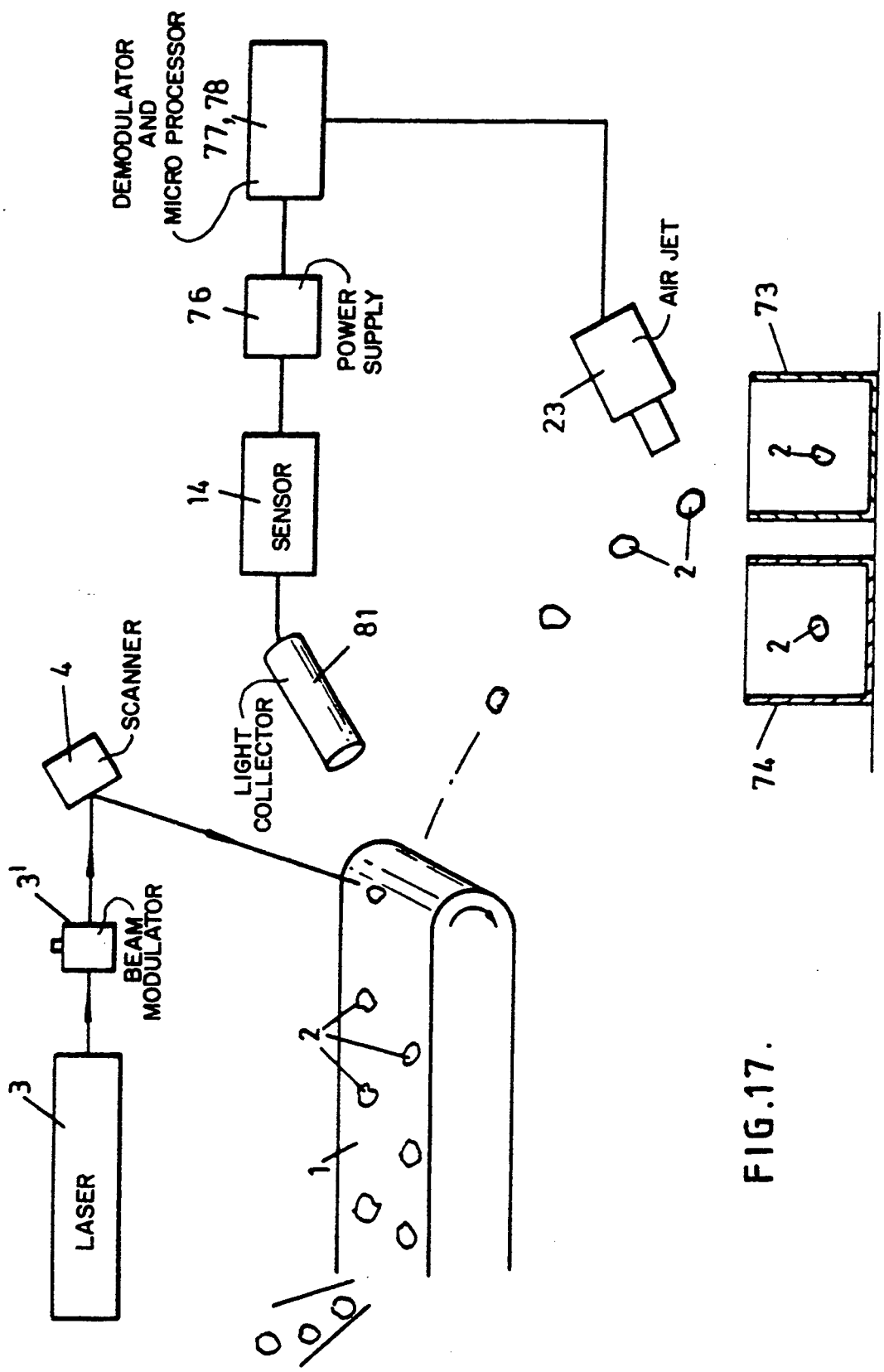
Figure 18:
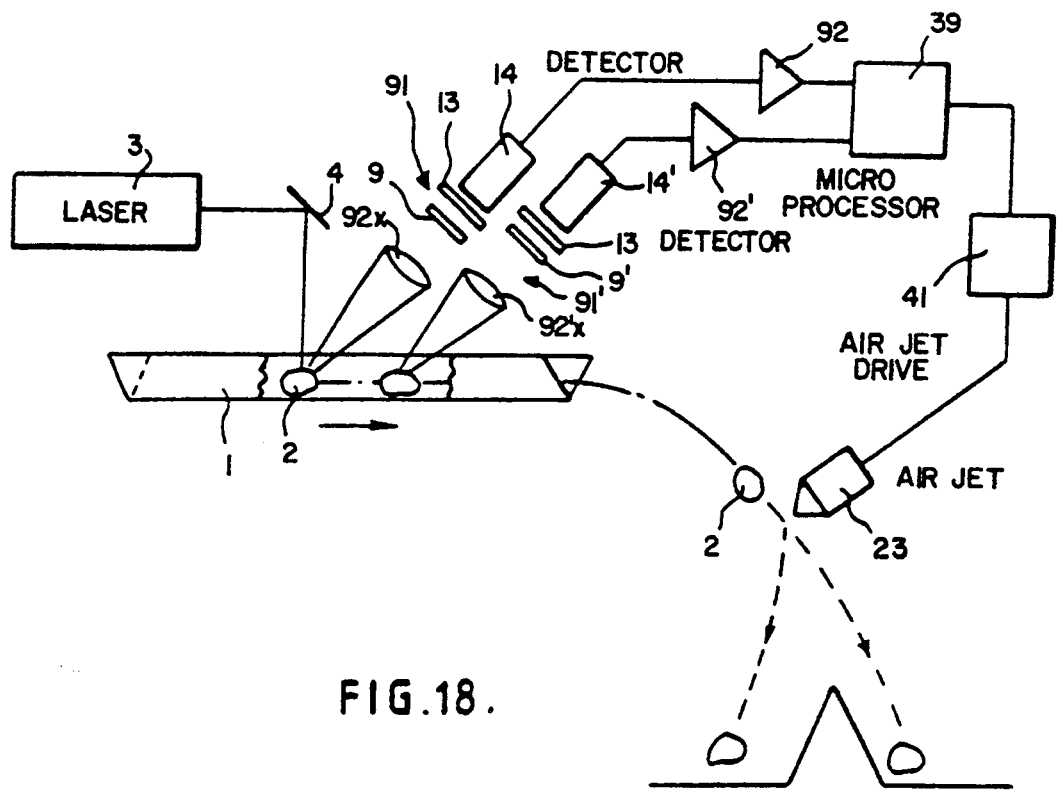
Figure 19:
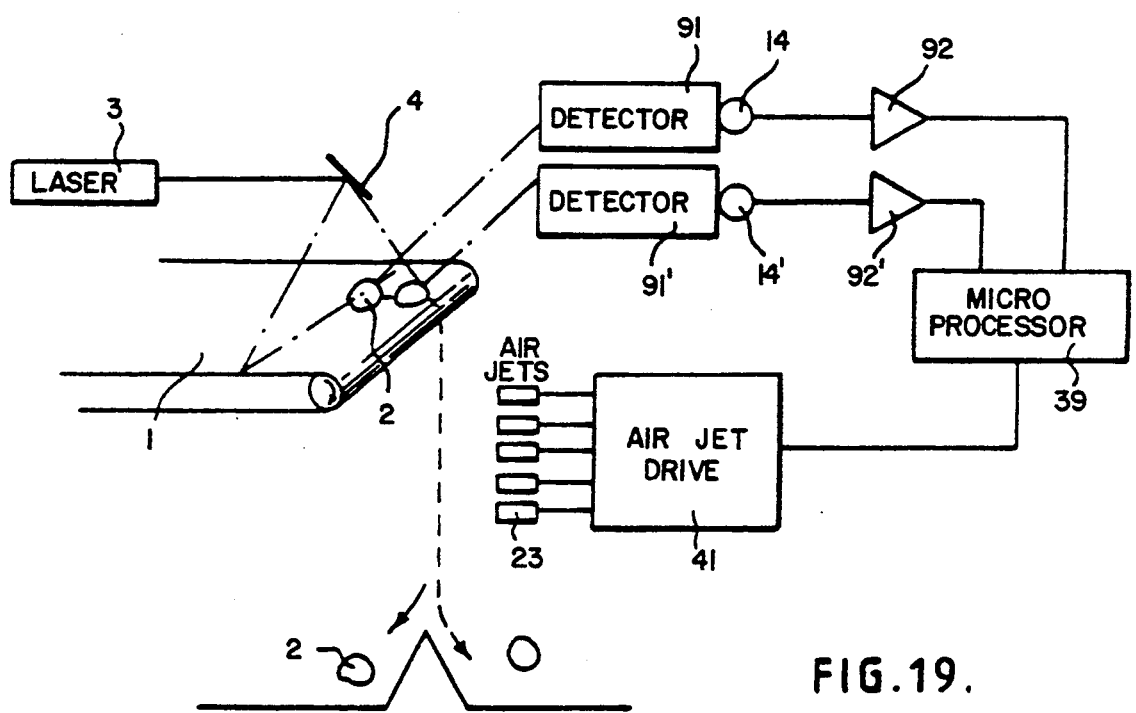

FIG. 6 is a schematic plan view of the end of the belt in FIG. 2:

FIG. 7 is a diagram of the apparatus of FIG. 2 and associated electronic components:

FIG. 8 corresponds to FIG. 2 but shows a second apparatus:

FIG. 9 is an isometric view of a possible collection means in FIG. 8:

FIG. 10 is a schematic view of a third apparatus:

FIG. 11 is a schematic view, taken at right angles to the view of FIG. 10:

FIG. 12 is a schematic, isometric view of part of a fourth apparatus:

FIG. 13 is a view looking down on the optical system of FIG. 12, also showing electronic components;

FIG. 14 is a schematic diagram illustrating the principle of the apparatus of FIGS. 16 and 17;

FIG. 15 is a schematic diagram illustrating the principle of operation of the apparatus of FIGS. 16 and 17;

FIG. 16 illustrates a fifth apparatus:

FIG. 17 illustrates a sixth apparatus;

FIG. 18 is a schematic view of a seventh apparatus:

FIG. 19 is a schematic view of an eighth apparatus: and

Figure 20:
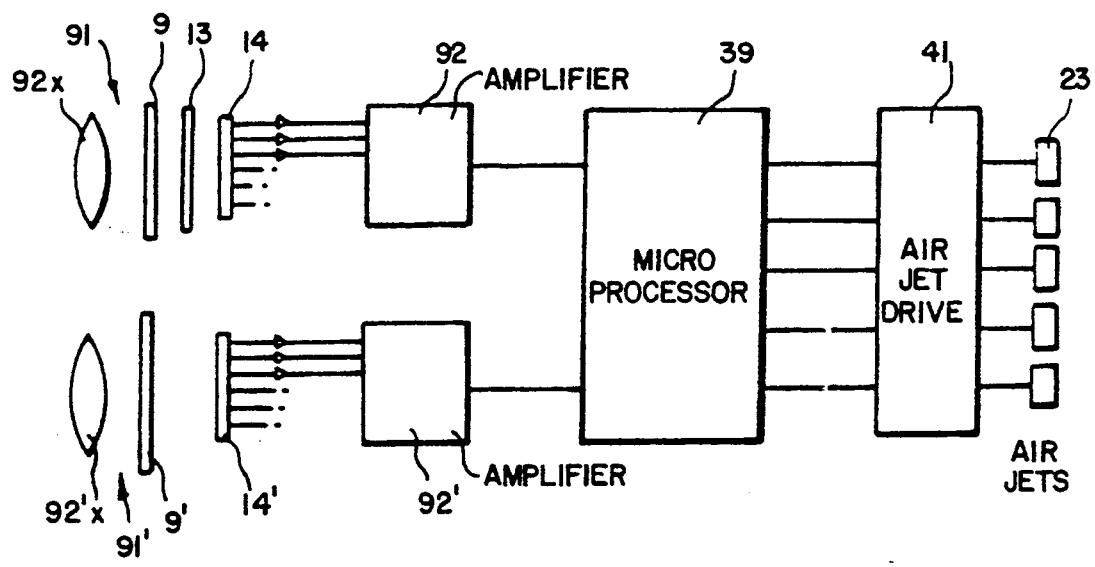

FIG. 20 is a schematic view of an alternative arrangement that can be incorporated in the apparatus of FIG. 19.

Throughout, the same references indicate the same or similar items. Variations discussed in relation to any embodiment can be applied to the other embodiments, if appropriate.

FIG. 1

Figure 1:
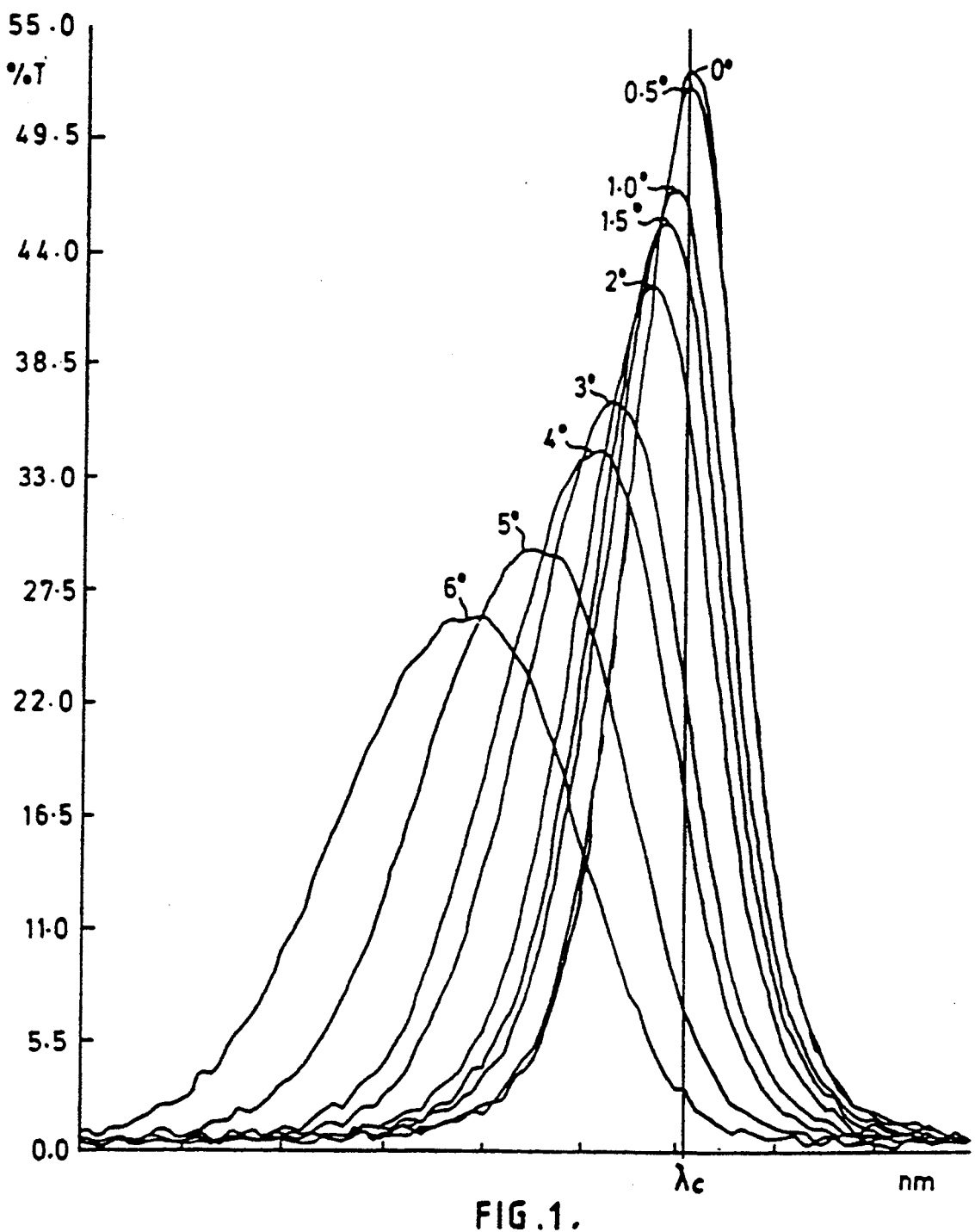
FIG. 1 is a graph of percentage transmitted energy (%T) against wavelength in nm, showing a set of curves for various angles of incidence for a narrow band pass filter of nominal value λ nm with a nominal band width of 1.4 nm at half maximum transmissivity.

FIG. 1 has been discussed above.

FIGS. 2-7

Figure 3:
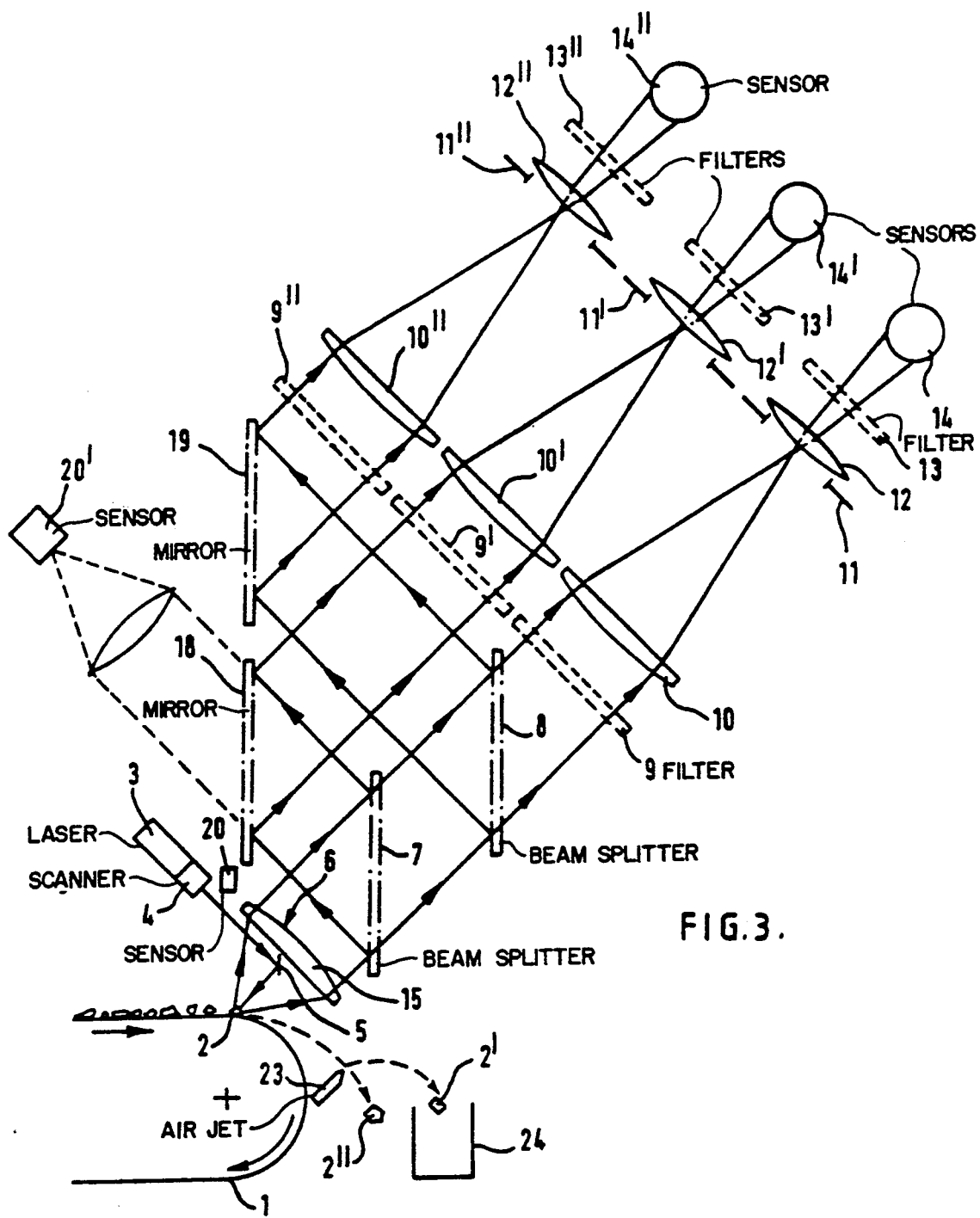
FIG. 3 is a schematic view, taken at right angles to the view of FIG. 1.

In FIGS. 2 and 3, a moving belt 1 (made of material which does not luminesce at the excitation frequency, i.e. at the frequency of the laser) is wide, i.e., of substantial width, and carries a single layer of ore or gangue particles or objects 2. In this way, the particles 2 are distributed widthwise over and move along a feed path whose width is capable of accommodating a number of the particles. The particles 2 have been formed by roll crushing, and have been screened so that they are in a predetermined size range. In general terms, it is preferred that the particles 2 should be of roughly similar sizes and suitable (plan view) occupancy on the belt 1 to reduce the effects of piling or shielding—one suitable occupancy is 5%, but it could vary for example from 4% to 80%. The sizing and occupancy can be arranged using known mechanical means.

A laser 3 projects exciting radiation along an extended line transversely of the belt 1. This can be achieved in any suitable way; for instance, the laser 3 can be scanned along the line using a scanning unit 4, in which case the laser 3 can be say a 2 watt laser. Other alternatives are possible, e.g. using a linear array of a multitude of laser diodes. The optics can be arranged in any suitable way and FIG. 3 is only schematic—preferably the laser 3 is effectively on the same optical axis as the viewing system described below, so that on each ore particle 2, the same point is illuminated and examined; for instance, a narrow, transverse mirror 5 can be used—other possibilities are discussed below. A separate viewing system can be added to examine, e.g. at 90° to the incident radiation, for instance to sense a diamond on the side of a larger lump of ore, though different focal lengths and lens widths may be required.

The line is examined with a viewing system having collection means in the form of a multi-lens array 6, beam splitters 7,8, a narrow band pass or line filter a converging lens 10, a telecentric stop 11, a field lens 12, a laser blocking filter 13 and a PMT 14, the PMT 14 being a sensing means and sensing the selected frequency radiation emitted by particles 2.

The filter 9 can be chosen to pass the Stokes signal or the anti-Stokes signal. A 2 nm or 1 nm band can be passed, centred on the signal in question. If the gangue is irradiated with an argon ion laser 3 operating at 514.5 nm, the principal Raman emissions of diamond consist of two sharp lines at 552.4 nm (the Stokes signal) and 481.5 nm (the anti-Stokes signal): if a helium neon laser 3 is used, operating at 632.8 nm, the principal Raman emissions of diamond consist of two sharp lines at 691.1 and 583.6 nm.

The collection means usually extends parallel to the irradiated line on the belt 1, and in effect has individual sections formed by an array of side-by-side converging elements or lenses 15 forming the multi-lens array 6. Each lens 15 is of rectangular shape as seen looking along the optical axis, arranged so that in the plane normal to the optical axis, the major axis of the lens 15 is at 90° to the irradiated line. The ore particles 2 are roughly at the focus of the lenses 15 so that each individual lens 15 provides roughly parallel rays from points on the particles 2. As can be seen in FIG. 3, each lens 15 has a long dimension parallel to the direction of movement of the belt 1, and thus captures a large amount of radiation coming from each particle, having an f number of 1 or less. As can be seen from FIG. 2, each lens 15 is narrow across the belt 1, having an f number of 7 or more. Thus each lens 15 receives a three-dimensional sector of emission from the particles 2 on the belt 1, which, as seen looking along the irradiated line, is substantially larger than as seen looking at 90° both to the line and to the optical axis. The roughly parallel rays are focused by the converging lens 10 roughly in the plane of the telecentric stop 11. As illustrated diagramatically in FIG. 2, the effect of this is (ideally) that rays which pass through a lens 15 which is not immediately above a particle 2 are stopped by the stop 11; FIG. 2 illustrates two ray bundles 16,17 from an object 2 which is nearly on the boundary between two lenses 15; the ray bundle 16 from the lens 15 above the object 2 is not stopped whereas the ray bundle 17 from the adjacent lens 15 is stopped. In practice, there may be a little overlap, a particle 2 nearly on the boundary being sensed through two lenses 15, but this need not matter though it gives rise to the periodicity referred to above. Thus the ray bundle having the greater angle of incidence on the filter 9 is stopped, and the viewing system can be arranged such that any ray having an angle of incidence greater than ±4° (or any specific, chosen angle) is stopped. In this way, as seen looking at 90° to the irradiated line, just a limited, relatively narrow sector of the radiation from each part of the line is sensed and analysed. The width of each lens 15 and the number of lenses 15 needed to cover the inspection zone is determined by the geometrical constraints outlined above; however, with lenses 15 of focal length 70 mm and a chosen acceptable filter angle of incidence of ±4°, 100 lenses 15 per metre width of belt are desirable. The optical axis of each individual lens 15 is substantially normal to the filter 9. The stop 11 can have a rectangular aperture, say 10 mm wide for examining a belt width of 300 mm.

In the other plane, looking along said line (FIG. 3), there is no problem with rays of high angles of incidence passing through the filter 9 as the radiation is emitted lust from one scan line across the belt 1—particles 2 on either side of the scan line are not irradiated and there are no off axis images.

The viewing system may pick up specular reflection of the laser radiation, of very great intensity compared to the Raman intensity. The laser blocking filter 13 is included as a significant amount of the laser wavelength will pass through the filter 9. The laser blocking filter 13 is not angularly dependent and can be placed anywhere in the optical system, but it is preferably placed immediately in front of the PMT 14 as only a smaller diameter is required in this plane. The laser blocking filter 13 can be a glass absorption filter and the amount of blocking can be chosen by choosing the correct thickness of glass.

Any number of beam splitters can be used in the optical system in order to abstract part of the radiation for specific purposes. As shown in any of FIGS. 4a, 4b and 4c, which are graphs of intensity (i) against frequency (f) for the emission of excited radiation by diamond, the Raman frequency $f_1$ (the Stokes signal or the anti-Stokes signal, whichever is chosen) is against a background radiation $i_b$ at the same frequency—the Raman radiation is lust a small blip in a luminescence spectra. Although it is not essential to subtract the background radiation, better sensing and higher accuracy are obtained if this is done. In effect, the background radiation is sensed at two different frequencies $f_2,f_3$ close on either side of the Raman frequency $f_1$, many relations of $f_1$, $f_2$ and $f_3$ may be used in a processing algorithm, one of which may be such that the signals of the frequencies $f_2,f_3$ are averaged, and the average is subtracted from the signal sensed at frequency $f_1$, thus distinguishing the Raman signal from the background signal. The frequencies $f_2,f_3$ can for example be 15 nm on each side. Using the beam splitters 7,8 and associated mirrors 18,19, part of the beam is directed into respective band pass filters 9',9", converging lenses 10',10", telecentric stops 11',11", field lenses 12',12", laser blocking filters 13',13" and PMT's 14',14". However any suitable geometric arrangement can be used. The band pass filters 9',9" pass the frequencies $f_2,f_3$. As the frequencies $f_2,f_3$ are not critical, a relatively wide band, e.g. 10 nm wide, can be sensed and the band pass filters 9',9" allow a correspondingly wide band of frequencies to pass; the band will be a multiple of the band passed by the filter 9. This arrangement means that the beam splitters 7,8 only need to split off just a small proportion, say 4% or 5% of the radiation.

Various techniques can be used to indicate or identify the particle 2 which emitted Raman radiation.

According to a first technique, a single PMT 14 can be used even if the belt 1 is very wide, scanning the exciting radiation with a scanning frequency which will depend upon the belt width and the speed and size of the particles; alternatively, a number of modules can be used with a corresponding number of PMT's, the same principle being employed in each module. If the exciting radiation is simply scanned, or if it is effectively scanned by spacing a number of time-division multiplexed lasers along the scanning line, a simple time domain technique indicates or identifies which particle 2 has emitted Raman radiation. FIG. 5 illustrates the signal from the PMT 14. Markers S, which can be adjustable physical stops or luminescing tracers, define the ends of the irradiated line (see FIG. 6) and give start and end registrations on the output signal. Knowing the start and end of scan, via the markers S, the location of the specific particle 2 is determined.

As a single, general technique, and particularly if the exciting radiation is not scanned (being e.g. X-radiation), it is possible to incorporate position-sensitive sensing means 20 or 20' sensitive to radiation such as general background luminescence (strong luminescence) emitted by diamonds and positioned such that the further sensing means 20 or 20' sense radiation which has not passed through the filter 9. Any Raman signal (weak luminescence) from a particle 2 detected by the PMT 14 indicates the presence in the irradiated line of a specific particle 2 to be sorted. The signal from the PMT 14 is passed (e.g. via an amplifier) to the module 39 and the positional signal from the sensing means 20 or 20' can be passed through an amplifier to a registration module which analyses the position of the signal from the sensing means 20 or 20' with respect to the width of the belt and gives a signal to the module 39 which includes time and position. When simultaneous signals are received from the PMT 14 and the sensing means 20 or 20', the air let control 41 (see below) actuates an appropriate air let 23 in accordance with the positional signal from the registration module and the specific particle 2 is blown out of its normal path.

The further sensing means 20 or 20' not only detect the presence of the specific particle 2 but also give a signal indicating its position. Thus a specific particle 2 is indicated when the PMT 14 and the sensing means 20 or 20' sense simultaneously. When sorting diamonds from ore, this can give a high confidence particle sort.

The further sensing means 20 may be a CCD camera or array or a position sensitive PMT.

A preferred arrangement is to have a scanned 1024 element CCD array 20 (or 20') behind a micro-channel plate signal intensifier, the information being taken off along a single channel by scanning or multiplexing. Very accurate positional information is given, but only a very simple optical system is required. Knowing the start and end of scan, via the markers S, the belt 1 can be sectioned in tracks according to groups of the CCD pixels, which groups can activate individual air lets 23 (see below).

The sensing means 20 can be provided with a laser line (narrow band) rejection filter for laser exciting radiation, or with a pass filter in the X-ray luminescence band (say 280 to 300 nm) for X-ray exciting radiation. However, if occupancy is being monitored, a laser pass filter is used for laser exciting radiation, to employ the laser wavelength.

As shown in FIG. 3, the sensing means 20 is preferably outside the viewing system, though (as shown in FIG. 3 at 20' as an alternative arrangement) it could be in the viewing system after the lens array 6, with a suitable beam splitter 18. As a further alternative, the sensing means 20' can be incorporated as well as the sensing means 20 and serve a different purpose, namely to view across the width of the belt 1 in order to monitor the occupancy of the belt 1: the occupancy can be altered by automatically changing the feed in a known way.

Using the second technique, an unscanned e.g. X-ray source 3 can be used to irradiate the line across the belt 1. Here the three channels of the module 6, 9—14 can have filters 9, 9', 9" of 1 or 2 nm width, allowing to pass the luminescent peak and the wavelength at full width half maximum points: as the diamond luminescence is distinguished by being semi-Gaussian, discrimination can be obtained, at least for specific types of diamond. The peak may be between 400 and 500 nm (depending on the luminescence mechanism of the specific type of diamond), and the filters 9', 9" 150 nm on either side of the peak.

According to a third technique, the sensing means 20 or 20' can be omitted. The scan line is scanned by a single laser 3, but the laser 3 is pulsed with a pulse frequency which is varied in some way across the scan; for instance it can be ramped from 1 MHz to 2 GHz from one end of the scan line to the other. When a diamond 2 is detected, a modulation burst is superimposed on the signal on the main PMT 14, due to the emission of Raman luminescence from the diamond 2. The frequency of response of the main PMT 14 corresponds to the position in the scan line from which the Raman luminescence is emitted. The frequency of response can be determined by a microprocessor which includes suitable electronics to demodulate the PMT signal and compare it with positional signals indicating the position of the source of the emitted signal, i.e. of the diamond 2. Heterodyne detection can be used, in the module 39 referred to below.

According to fourth, fifth and sixth techniques, the method described below with reference to FIGS. 12 and 13, FIGS. 14 to 17 and FIGS. 18 to respectively, can be used.

The system shown in FIGS. 2 to 7 has three channels, namely a main detection channel for one of the Raman frequencies, and two side channels. For more accurate sorting, more channels could be used, for example a further main detection channel for a different frequency emitted signal and its own two side channels.

In some arrangements, there is no need of the beam splitters or other arrangements for subtracting background radiation. In some cases, all diamonds except type IIb diamonds can be distinguished by their luminescence—type IIb diamonds do not luminesce but do emit Raman radiation. Using a rather wider band pass filter 9 (which however still gives angle of incidence problems) and a laser blocking filter 13, all the diamonds can be indicated or identified.

It is possible to place a broad pass band filter in front of the narrow pass band filters 9, 9', 9", e.g. to select a broad band with a Raman frequency in the middle.

Any of the components in the viewing system can be replaced by equivalent components—for instance, holographic plates or mirrors or parabolic concentrators can be used instead of ordinary or Fresnel lenses; the field lenses 12, 12' and 12" could as a further alternative be replaced by inclined mirrors or light tubes. Precise focussing is not required, only the collection of the appropriate photons.

The optics of the laser 3 may be different. For instance, the mirror 5 could be behind the collection lenses 15, or an aluminised strip could be provided on the beam splitter 7 with a gap formed in the mirror 18: in such a case, a long slot can be formed in the collection lens array 6, or the lens array 6 can be used to focus the laser beam cylindrically along the scan line.

FIG. 6 illustrates a monitoring means for self-calibration on-line (i.e. without stopping sorting), or for giving a signal to indicate that there is a malfunction. A line S—S is scanned on the belt 1 from point S to point S. On each side of the belt 1 there are first zones represented by tracer stones 21, which may be made of synthetic diamonds mixed with epoxy resin, on one side of the belt 1 there are two second zones or beam dumps in the form of holes 22 which absorb all radiation. Using a suitable detector, e.g. the CCD camera 20' shown in FIG. 3, the radiation from the tracer stones 21 and holes 22 can be sensed and processed to give signals, automatically, e.g. to increase or decrease the gain of the PMT's 14, 14' and 14". The signals generated by the tracer stones 21 and holes 22 can be integrated over say 6 seconds to reduce random effects.

FIG. 3 illustrates schematically a row of air lets 23 for selecting (i.e. indicating or identifying) diamonds 2' by blowing them out of the trajectory followed by non-diamond material 2", a diamond-receiving bin 24 being schematically indicated; naturally any other particle that also meets the selected criteria will also be selected.

FIG. 7 illustrates the identification and control system. The following further items are illustrated in FIG. 7, but their function and interconnection need not be described in detail: laser drive and shutter control 31, scan (polygon) motor drive 32, beam splitter 33, grating 34 and associated lens system, photo sensor 35, start and end of scan detectors 36, 37, belt speed encoder 38, measurement and test module 39 (a microprocessor), test light emitting diodes 40, and air let control system 41.

Any suitable scan frequency can be used for the radiation. The scan will normally be simple direction without fly-back, e.g. using a rotating 64 facet polyhedric mirror as the scanning unit 4. Assuming point focus (which could be in a plane spaced above the belt at half the expected particle height), a 133 Hz scan at a belt speed of 1.6 m/s and with a 300 mm scan width gives ½ mm resolution, suitable for 1 mm particles; a 400 Hz scan at a belt speed of 5 m/s and with a 1000 mm scan length gives 1 mm resolution, suitable for 3 mm particles.

If the belt 1 is very wide, two or more lasers 3 and/or two or more of the optical modules 6 to 14 can be used side-by-side.

FIGS. 8 and 9

FIG. 8 corresponds to FIG. 2 and items performing the same functions are referenced with the same references and not further explained. The most significant difference is that a cylindrical lens 6' is used instead of the multi-lens array 6 of FIGS. 2 and 3. FIG. 3 shows the arrangement of FIG. 8, as seen looking along the line. The lens 6' can be aspheric and/or a Fresnel lens, a Fresnel lens being shown in FIG. 9, and corrects aberrations and increases the f No.

The stop 11 is in the focal plane of the lens 10, which is a normal spherical lens. This means that as seen looking along said line (FIG. 3), the rays are focussed in the plane of the stop 11, whereas as seen looking at 90° to said line (FIG. 8), the rays are focussed behind the plane of the stop 11. Nonetheless, as seen from the ray bundle shown in FIG. 8, the stop 11 stops out any rays which have an angle of incidence greater than a predetermined maximum on the narrow band pass filter 9.

With a cylindrical lens 6' of focal length 70 mm, it is possible to have a depth of focus of approximately ±10 mm. The depth of focus can be increased if the length and size of the optical system is increased.

FIGS. 10 and 11

There is a collection means extending parallel to the irradiated line on the belt 1, and comprising a cylindrical lens 51 and an acrylic light pipe (also known as a light tube, line array system or a concentration collection assembly) 52. The cylindrical lens 51 can be a Fresnel lens, and need not be of circular cross-section. The lens 6 collects and focuses the light emitted from the objects 2 on the line, forming a line image at the input of the light pipe 52, acting as a light guide. The light pipe 52 is merely a fan-shaped arrangement of reflecting partitions with a top and bottom. This translates the line image into a circular image at the output end of the light pipe 52, but the light leaving the light pipe 52 leaves at all angles of incidence—the cylindrical lens 51 should be positioned at such a distance from the particles 2 that it maximises energy collection (as seen in the plane of FIG. 11) into the light pipe 52. The light is collected by a compound parabolic concentrator (CPC) 53, which, as shown in FIG. 2, collects the light from one focus 54, collimates it within the CPC, i.e. forms the rays into a bundle of roughly parallel rays, and re-focuses it at the second focus 55. The narrow band pass filter or line filter 9 is placed in the centre plane of the CPC 8, normal to the optical axis, i.e. within the region of roughly parallel light.

The filter 9 can be as described above in relation to FIGS. 2 to 7.

The CPC 8 is followed by the laser blocking filter 13 and a photo-multiplier tube (PMT) 14.

As in FIGS. 2 to 7, in the other plane, illustrated in FIG. 11, there is no problem with rays of high angles of incidence passing through the line filter 11.

As in FIGS. 2 to 7, any number of beam splitters can be used in the optical system in order to abstract part of the radiation for specific purposes, and any suitable geometric arrangement can be used.

For more accurate sorting, more channels could be used, for example a further main detection channel for a different frequency emitted signal and its own two side channels.

As discussed above, there may be no need of the beam splitters or other arrangements for subtracting background radiation.

Various techniques can be used to indicate or identify the particle 2 which emitted Raman radiation, as described above with reference to FIGS. 2 to 7.

As mentioned in relation to FIGS. 2 to 7, it is possible to place a broad pass band filter in front of the narrow pass band filters 9, 9', 9", e.g. to select a broad band with a Raman frequency in the middle.

Any of the components in the viewing system can be replaced by equivalent components—for instance, holographic plates or mirrors or parabolic concentrators can be used instead of ordinary or Fresnel lenses. The light pipes 7, 7', 7" could as a further alternative be without internal fan-shaped walls, or be replaced by two inclined mirrors, or by bundles of fibres, e.g. of decreasing cross-section. The CPC's 8, 8', 8" could be without their second half, other optics being used behind the filters 9, 9', 9" The CPC's 8, 8', 8" could be just two parallel plates in the section of FIG. 3. Precise focussing is not required, only the collection of the appropriate photons.

The optics of the laser 3 may be different, as mentioned in relation to FIGS. 2 to 7. Monitoring means for self-calibration on-line can be included, as described in relation to FIGS. 2 to 7.

FIGS. 12 and 13

In an alternative system, say with X-radiation, the sensing means 20 described above with reference to FIGS. 2 to 7 can be used alone without the remainder of the optical systems, though with suitable filtering, to detect luminescence, which need not be Raman and can be e.g. broad band luminescence. However, a preferred system is shown in FIGS. 12 and 13.

The embodiment illustrated in FIGS. 12 and 13 is much simpler than that specifically described in FIGS. 2 to 7.

A line of X-ray radiation is projected transversely across the belt 1 using any suitable X-ray device 3, and the luminescence, if any, of the particles 2, is detected after the particles 2 have been projected off the end of the belt 1, along a line S-S indicated in FIG. 12. The detection uses the simple optical apparatus illustrated in FIG. 13, comprising a lens system 61 and a PMT 62. The PMT 62 is connected through amplifier 63 to a micro-processor 39 in turn connected to air jet drives 41 which energise one of a number of air jets 23 distributed across the width of the path of the particles 2, in order to blow out of the path into a sort bin any particle selected by the micro-processor 39.

AS represented in FIG. 13, the image of the luminescing particle 2 is focused on the detecting plane of the PMT 62. The PMT 62 is scanned to determine whether there is an image on the detecting plane, in other words the detecting means is scanned across the particles 2, and a simple time domain technique indicates or identifies which particle 2 has emitted the luminescence. The signal from the PMT 62 will generally be as in FIG. 5.

Any suitable scanning frequency can be used for scanning the PMT 6. For instance with a 1 m wide conveyor travelling at 3 m/s, 400 Hz is suitable; with a 300 mm wide conveyor 1 travelling at 1.6 m/s, 133 Hz is suitable.

As an alternative to using the scanned PMT 6, a scanned CCD array can be used, for instance a scanned 1024 element CCD array behind a micro-channel plate signal intensifier. Knowing the start and end of scan, via the markers S, the path of the particles 2 can be sectioned or divided into tracks according to groups of the CCD pixels, which groups can activate individual air jets 23. The CCD array can have a fixed internal clock, being scanned at say 2 MHz.

FIGS. 14 and 15

FIG. 14 shows three schematic graphs of intensity against time, $R_i$ being the incident, exciting radiation, $R_e$ being the emitted radiation and D being the detection. In the $R_e/t$ graph, $R_{e1}$ is the Raman emission and $R_{e2}$ is fluorescence.

The constant wave length exciting radiation is pulsed as in the $R_i/t$ graph and the detector is activated, or its output signal is chopped, as in the D/t graph. It will be seen that the detector is effective when the Raman emission $R_{e1}$ is near its maximum and the other luminescent radiation $R_{e2}$ has not risen so far as to interfere with the detection of the Raman emission $R_{e1}$, i.e. the detector does not effectively detect emitted radiation which has a substantially longer rise time than the Raman emission $R_{e1}$. By keeping the pulse length short relative to the pulse frequency, the intensity of the other luminescence remains low and the Raman emission is either of greater intensity than the other luminescence, or at least of sufficient intensity to be detectable.

FIG. 15 shows, on a much longer time scale t, the exciting radiation $R_1$ and the emitted radiation $R_e$ when a diamond is detected, i.e. when the scan passes over a diamond. The detector signal will be similar to that of the emitted radiation. The modulation burst indicates Raman emission and hence the presence of the diamond. The Raman emission can be distinguished by suitable thresholding which removes the background signal caused by other luminescence, or can be distinguished by heterodyne detection or any suitable demodulation electronics.

FIG. 16

FIG. 16 shows a simple practical arrangement, in which a V-belt 71 is used as a single particle feeder (a similar single particle feeder such as a pick-up wheel may be used). The objects or particles 2 are fed onto the belt 71 in any suitable way, and at the end of the belt pass through a beam projected by a laser 3 with an optical laser beam modulator 3'. The modulator 3' modulates the beam in a generally sinusoidal manner. At the point where the beam strikes the particles 2, the particles 2 are examined by an optical collection system 72 and a detector 14 in the form of a PMT. Suitable filters are incorporated, a laser wavelength blocking filter 13 and a narrow band pass filter 9 being shown. As the particles 2 are projected off the end of the belt 1, they pass suitable ejection means, shown as an air jet 23. Reject particles 2 (which would be the vast majority in the case of gangue sorting) do not cause the air jet 9 to be operated and pass into a reject bin 73. Selected particles cause the air jet 23 to be operated and are blown out of their normal trajectory into a sort bin 74.

In one embodiment using a 2 watt argon ion laser 3, the laser wavelength is 514.5 nm, modulated at a frequency of 1 GHz. 552.4 nm Raman emission (the diamond Stokes emission) can be observed using a 1 nm wide band pass for the filter 8, provided the background is subtracted by ratioing the backgrounds at 537 and 567 nm generally as described above. Alternatively, a 5 nm band can be used for the pass filter 8, with no background subtraction. It is believed possible, and may be preferable, to observe the 481.5 nm anti-Stokes emission, in a similar manner. The modulator 31 can be a Bragg cell, or the laser 3 and modulator 31 can be replaced by a mode-locked laser. The PMT 14 can be a microchannel plate PMT, which has a very fast rise time.

Another embodiment uses a helium-neon laser operating at 632.8 nm, its principal Raman emissions for diamond consist of two sharp lines at 691.1 nm (Stokes) and 583.6 nm (anti-Stokes).

The electronic circuitry includes a demodulator drive 75 for the beam modulator 4, an amplifier/power supply unit 76, a demodulator 77 for the signal from the PMT 14, and a microprocessor 78 with the necessary logic for identifying the Raman emissions from e.g. diamonds and activating the jet 23.

FIG. 17

In FIG. 17, the beam from the laser 3 is scanned across a wide belt 1 using a suitable scanning system 4 (e.g. a galvonometer or rotating polygon). In this way, the laser beam is scanned across the belt 1 just before the particles 2 are projected off the belt. A suitable light collecting system 81 is used. The system 81 has a wide aperture and a narrow band pass filter with the optics arranged so that the angle of incidence on the filter is within acceptable limits. FIGS. 2 to 7 above disclose one suitable system.

FIGS. 18 to 20

In general, each embodiment has two optical detection modules 91, 91', each of which comprises an efficient optical signal collection system schematically represented at 6, 6', a narrow band pass filter 9, 9', a blocking filter 13' for the exciting radiation, and a detector 14, 14'. The optical signal collection system can be the system described with reference to FIGS. 2 to 7. The detector 14, 14' can be any suitable detector, such as a PMT or a diode. Each detector 14, 14' is selected and operated in a mode to enhance its time resolution characteristics. The detectors 14, 14' are connected through amplifiers 92, 92' to a microprocessor 39 whose output signal is passed to an air jet logic 41 which actuates one or more air jets 23 to eject the required particle 2 from its normal trajectory.

The first module 91 detects the signal given by the particle 2 during excitation. The second module 91' detects the signal, if any, from the same particle 2 (i.e., from the same zone) after the particle 2 has passed through the exciting radiation. A decision is made on the two signals in the microprocessor 39, whether the particle 2 is of interest and should be ejected. In one specific arrangement, the Raman luminescence (preferably the Stokes, though the anti-Stokes may be usable and better) is detected by the first module 91 and the broad band fluorescence background is detected by the second module 91'. The signal given by the second module 91' is subtracted from the signal given by the first module 91, to determine if Raman radiation is present on the signal detected by the first module 91.

In an alternative arrangement, using different narrow band pass filters 9, 9', different wavelengths can be detected by first and second modules 91, 91'.

FIG. 18 shows an arrangement in which a fast-moving V-belt 1 confines gangue particles 2 on the belt 1 to travel along a straight line (as seen in plan). The irradiating means 3, which may be a laser, illuminates a spot in the centre of the belt 1.

FIG. 19 shows an arrangement in which a wide belt 1 is used. A line across the belt is irradiated using the means 4 which can be a scanner provided with an encoder connected to the microprocessor 39, or (particularly if the radiation is X-ray, for instance a tungsten target X-ray tube operating at 40 key), merely spreads the radiation along a transverse line. The optical modules 6, 6' examine the whole width of the belt 1 and detect the position of the required particle 2 across the belt, the appropriate air jet 23 being energised.

FIG. 20 shows an arrangement in which the optical systems 91, 91' can be much simpler, the detectors 14. 14' being intensified CCD arrays each inspecting a section of, or track along, the belt 1 and aligned with the corresponding CCD element of the other optical system. The individual CCD elements are connected through amplifiers 92 in a conventional manner so as to be able to give positional signals.

The time interval between the two detection modules 91, 91' will depend upon the luminescence being detected and analysed, but one arrangement provides an interval of 0.1–0.5 seconds, with a belt speed of 1–5 ms and the modules 0.5 m apart. The time interval will depend upon physical limitations in designing the apparatus. The distance apart can be 50 nm, achievable using mirrors.

Beam splitters (not shown) and additional optical channels can be incorporated to enable a number, say three, of different wavelength bands to be examined for attenuation.

Examples

This can be carried out using the apparatus of FIG. 18. The first module 91 detects anti-Stokes Raman from diamonds and the second module 91' detects broad band luminescence from diamonds. Belt speeds are 1.6 m/s for Example 1 and 3 m/s for Example 2. The laser (Argon ion) wavelength is 514.5 nm. Filters 9, 9' are centred at 552.4 nm with a pass band of 1 or 2 nm. For sorting, a signal at the first module 91 and not at the second module 91' indicates Raman and hence diamond; a signal at the first module 91 and also at the second module 91' indicates luminescence and (usually) not diamond—most diamonds have a luminescence which is short compared to that of gangue materials.

The present invention has been described above purely by way of example, and modifications can be made within the spirit of the invention.

We claim:

1. A method of identifying a diamond or other specific luminescing mineral, comprising irradiating the diamond or mineral with high-frequency-modulated radiation of substantially constant wave length, thereby causing anti-Stokes radiation to be emitted from the diamond or mineral, and isolating the emitted anti-Stokes radiation from any emitted radiation having a long rise and/or decay time by detecting emitted radiation which is modulated at a frequency corresponding to the frequency of modulation of said modulated radiation.

2. A method of identifying diamonds or other specific luminescing minerals among ore particles moving in a path whose width can accommodate a number of the particles, comprising:
   irradiating a line across said path with high-frequency-modulated radiation of substantially constant wave length, thereby causing anti-Stokes radiation to be emitted from the diamonds or minerals; and
   isolating the emitted anti-Stokes radiation from any emitted radiation having a long rise and/or decay time by detecting emitted radiation which is modulated at a frequency corresponding to the frequency of said modulated radiation.

3. A method of identifying a diamond or other specific luminescing mineral, comprising irradiating the diamond or mineral with high-frequency-modulated radiation of substantially constant wave length, thereby causing Raman radiation to be emitted from the diamond or mineral, and isolating the emitted Raman radiation from any emitted radiation having a long rise and/or decay time by detecting emitted radiation which is modulated at a frequency corresponding to the frequency of modulation of said modulated radiation using a detector having a rise time response of about 0.2 ns.

4. A method of identifying a diamond or other specific luminescing mineral, comprising irradiating the diamond or mineral with high-frequency-modulated radiation of substantially constant wave length, thereby causing Raman radiation to be emitted from the diamond or mineral, isolating the emitted Raman radiation from any emitted radiation having a long rise and-/or decay time by detecting emitted radiation which is modulated at a frequency corresponding to the frequency of modulation of said modulated radiation, and using the method in the sorting of diamonds or other specific luminescing minerals from ore particles moving in a path whose width can accommodate a number of the particles by irradiating a line across said path with said modulated radiation, viewing all or an extended part of said line using narrow band pass filter means which, within a specific angle of incidence, substantially filter out all but said Raman radiation, and sensing with sensing means radiation which passes through said filter means, rays outside said angle of incidence being prevented from reaching said sensing means.

5. A method of identifying diamonds or other specific luminescing minerals among ore particles moving in a path whose width can accommodate a number of the particles, comprising:
irradiating a line across said path with high-frequency-modulated radiation of substantially constant wave length, thereby causing Raman radiation to be emitted from the diamonds or minerals; and
isolating the emitted Raman radiation from any emitted radiation having a long rise and/or decay time by detecting emitted radiation which is modulated at a frequency corresponding to the frequency of said modulated radiation using a wide aperture viewing system with narrow band pass filtering.

6. A method of identifying diamonds or other specific luminescing minerals among ore particles moving in a path whose width can accommodate a number of the particles, comprising:
irradiating a line across said path with high-frequency-modulated radiation of substantially constant wave length, thereby causing Raman radiation to be emitted from the diamonds or minerals; and
isolating the emitted Raman radiation from any emitted radiation having a long rise and/or decay time by detecting emitted radiation which is modulated at a frequency corresponding to the frequency of said modulated radiation using a detector having a rise time response of about 0.2 ns.

7. Apparatus for identifying diamonds or other specific luminescing minerals which are irradiated with high-frequency-modulated radiation of substantially constant wave length and for sorting such diamonds or other luminescing minerals from ore particles moving in a path whose width can accommodate a number of the particles, thereby causing Raman radiation to be emitted from the diamonds or minerals, the apparatus comprising means for isolating the emitted Raman radiation from any emitted radiation having a long rise and/or decay time by detecting emitted radiation which is modulated at a frequency corresponding to the frequency of modulation of said modulated radiation, means for projecting said modulated radiation onto said diamonds or minerals, said isolating means comprising viewing means for viewing all or an extended part of said line, and said viewing means comprising narrow band pass filter means which, within a specific angle of incidence, substantially filter out all but said Raman radiation, sensing means for sensing radiation which passes through said filter means, and preventing means for preventing rays outside said angle of incidence from reaching said sensing means.

8. The apparatus of claim 7, further comprising means for moving the ore particles in a path whose width can accommodate a number of the particles, and means for irradiating a line across said path with said modulated radiation.

9. Apparatus for identifying diamonds or other specific luminescing minerals which are irradiated with high-frequency-modulated radiation of substantially constant wave length, thereby causing Raman radiation to be emitted from the diamonds or minerals, the apparatus comprising means for isolating the emitted Raman radiation from any emitted radiation having a long rise and/or decay time by detecting emitted radiation which is modulated at a frequency corresponding to the frequency of modulation of said modulated radiation, said isolating means including a detector having a rise time response of about 0.2 ns.

10. Apparatus for identifying diamonds or other specific luminescing minerals which are irradiated with high-frequency-modulated radiation of substantially constant wave length, thereby causing anti-Stokes radiation to be emitted from the diamonds or minerals, the apparatus comprising means for isolating the emitted anti-Stokes radiation from any emitted radiation having a long rise and/or decay time by detecting emitted radiation which is modulated at a frequency corresponding to the frequency of modulation of said modulated radiation.

11. Apparatus for identifying diamonds or other specific luminescing minerals among ore particles moving in a path whose width can accommodate a number of the particles, and across which path a line is irradiated with high-frequency-modulated radiation of substantially constant wave length, thereby causing Raman radiation to be emitted from the diamonds or minerals, the apparatus comprising means for isolating the emitted Raman radiation from any emitted radiation having a long rise and/or decay time by detecting emitted radiation which is modulated at a frequency corresponding to the frequency of modulation of said modulated radiation, said isolating means including a wide aperture viewing system including narrow band pass filtration.

12. Apparatus for identifying diamonds or other specific luminescing minerals among ore particles moving in a path whose width can accommodate a number of the particles, and across which path a line is irradiated with high-frequency-modulated radiation of substantially constant wave length, thereby causing Raman radiation to be emitted from the diamonds or minerals, the apparatus comprising means for isolating the emitted Raman radiation from any emitted radiation having a long rise and/or decay time by detecting emitted radiation which is modulated at a frequency corresponding to the frequency of modulation of said modulated radiation, said isolating means comprising a detector having a rise time response of about 0.2 ns.

13. Apparatus for identifying diamonds or other specific luminescing minerals among ore particles moving in a path whose width can accommodate a number of the particles, and across which path a line is irradiated with high-frequency-modulated radiation of substantially constant wave length, thereby causing anti-Stokes radiation to be emitted from the diamonds or minerals, the apparatus comprising means for isolating the emitted anti-Stokes radiation from any emitted radiation having a long rise and/or decay time by detecting emitted radiation which is modulated at a frequency corresponding to the frequency of modulation of said modulated radiation.

14. The apparatus of claim 13, and further comprising means for projecting said modulated radiation onto said ore particles.

15. The apparatus of claim 13, further comprising means for moving the ore particles in a path whose width can accommodate a number of the particles, and means for irradiating a line across said path with said modulated radiation.

* * * * *